US012582300B2

(12) United States Patent
Thissen et al.

(10) Patent No.: US 12,582,300 B2
(45) Date of Patent: Mar. 24, 2026

(54) STEERABLE INSTRUMENT COMPRISING A DETACHABLE PART

(71) Applicant: Fortimedix Assets II B.V., Geleen (NL)

(72) Inventors: Mattheus Hendrik Louis Thissen, Swalmen (NL); Marcel Antonius Elisabeth Verbeek, Voerendaal (NL)

(73) Assignee: Fortimedix Assets II B.V., Geleen (NL)

( * ) Notice: Subject to any disclaimer, the term of this patent is extended or adjusted under 35 U.S.C. 154(b) by 881 days.

(21) Appl. No.: 17/599,633

(22) PCT Filed: Apr. 7, 2020

(86) PCT No.: PCT/NL2020/050238
§ 371 (c)(1),
(2) Date: Sep. 29, 2021

(87) PCT Pub. No.: WO2020/218920
PCT Pub. Date: Oct. 29, 2020

(65) Prior Publication Data
US 2022/0061634 A1    Mar. 3, 2022

(30) Foreign Application Priority Data

Apr. 8, 2019   (NL) ..................................... 2022896
Oct. 11, 2019   (NL) ..................................... 2023998

(51) Int. Cl.
*A61B 1/005*     (2006.01)
*A61B 17/00*     (2006.01)
(Continued)

(52) U.S. Cl.
CPC .......... *A61B 1/0057* (2013.01); *A61B 1/0052* (2013.01); *A61B 17/00234* (2013.01);
(Continued)

(58) Field of Classification Search
CPC .......... A61M 25/0133; A61M 25/0136; A61B 34/71; A61B 2034/715; A61B 2034/301;
(Continued)

(56) References Cited

U.S. PATENT DOCUMENTS 2,515,366 A   7/1950   Zublin
2,717,146 A   9/1955   Zublin
(Continued)

FOREIGN PATENT DOCUMENTS

CH        81017 A    5/1919
CN    101522121 A    9/2009
(Continued)

OTHER PUBLICATIONS

International Search Report and Written Opinion mailed Feb. 8, 2021, International Application No. PCT/NL2020/050238, 28 pages.

*Primary Examiner* — Devin B Henson
(74) *Attorney, Agent, or Firm* — Fortem IP LLP

(57) ABSTRACT

A steering device for connecting to an elongated instrument comprises a locking plate with a coupling to which a steering plate of the instrument can secure such that the steering plate and the locking plate move together; and a steering unit for moving the locking plate. The elongated instrument comprises a plurality of elongated elements extending along an instrument shaft and secured to a steering plate at a proximal end of the instrument shaft, with the steering plate being movably connected around a support member secured to the shaft.

17 Claims, 12 Drawing Sheets

(51) Int. Cl.
    *A61B 34/00*          (2016.01)
    *A61B 34/30*          (2016.01)
(52) U.S. Cl.
    CPC .... *A61B 34/71* (2016.02); *A61B 2017/00323* (2013.01); *A61B 34/30* (2016.02)
(58) Field of Classification Search
    CPC ............... A61B 1/0052; A61B 1/0057; A61B 2017/00323
    See application file for complete search history.

(56)             References Cited

U.S. PATENT DOCUMENTS

| | | | |
|---|---|---|---|
| 3,788,304 A | 1/1974 | Takahashi | |
| 4,362,520 A | 12/1982 | Perry | |
| 4,706,659 A | 11/1987 | Matthews et al. | |
| 4,745,908 A | 5/1988 | Wardle | |
| 5,271,381 A | 12/1993 | Ailinger et al. | |
| 5,749,828 A | 5/1998 | Solomon et al. | |
| 5,807,241 A | 9/1998 | Heimberger | |
| 5,928,136 A | 7/1999 | Barry | |
| 6,107,004 A | 8/2000 | Donadio, III | |
| 6,450,948 B1 | 9/2002 | Matsuura et al. | |
| 6,890,329 B2 | 5/2005 | Carroll et al. | |
| 7,189,228 B2 | 3/2007 | Eum et al. | |
| 7,320,700 B2 | 1/2008 | Cooper et al. | |
| 7,553,275 B2 | 6/2009 | Padget et al. | |
| 7,615,067 B2* | 11/2009 | Lee | A61B 1/0057 |
| | | | 606/205 |
| 8,257,267 B2 | 9/2012 | Thornton | |
| 8,323,241 B2 | 12/2012 | Salahieh et al. | |
| 8,327,518 B2 | 12/2012 | Eberhard | |
| 8,382,742 B2 | 2/2013 | Hermann et al. | |
| 8,398,587 B2 | 3/2013 | Dewaele et al. | |
| 8,708,954 B2 | 4/2014 | Webler | |
| 8,740,884 B2 | 6/2014 | Verbeek | |
| 8,845,522 B2 | 9/2014 | McIntyre et al. | |
| 8,882,680 B2 | 11/2014 | Furlong et al. | |
| 8,986,317 B2 | 3/2015 | Verbeek | |
| 9,072,505 B2 | 7/2015 | Furlong et al. | |
| 9,138,566 B2 | 9/2015 | Cabiri | |
| 9,174,024 B1* | 11/2015 | Romoscanu | A61B 34/30 |
| 9,198,561 B2 | 12/2015 | Smith et al. | |
| 9,220,398 B2 | 12/2015 | Woodley et al. | |
| 9,339,271 B2 | 5/2016 | Ranucci et al. | |
| 9,421,343 B2 | 8/2016 | Berthiaume et al. | |
| 9,462,932 B2 | 10/2016 | Ostrovsky et al. | |
| 9,468,359 B2 | 10/2016 | Weisshaupt et al. | |
| 9,655,637 B2 | 5/2017 | Mueller | |
| 9,848,858 B2 | 12/2017 | Verbeek | |
| 9,877,720 B2 | 1/2018 | Worrell et al. | |
| 10,010,246 B2 | 7/2018 | Quaye | |
| 10,265,087 B2 | 4/2019 | Furlong et al. | |
| 10,405,876 B2 | 9/2019 | Boudreaux | |
| 10,420,537 B2 | 9/2019 | Salahieh et al. | |
| 10,441,746 B2 | 10/2019 | Besselink | |
| 10,449,010 B2 | 10/2019 | Dewaele et al. | |
| 10,456,556 B2 | 10/2019 | Cabiri | |
| 10,485,579 B2 | 11/2019 | Lenker | |
| 10,492,771 B2 | 12/2019 | Nunan | |
| 10,500,373 B2 | 12/2019 | Barrish et al. | |
| 10,524,868 B2 | 1/2020 | Cooper et al. | |
| 10,542,878 B2 | 1/2020 | Dewaele et al. | |
| 10,561,467 B2 | 2/2020 | Van Der Linde et al. | |
| 10,603,047 B2 | 3/2020 | Ding et al. | |
| 10,646,104 B1 | 5/2020 | Sinay et al. | |
| 10,729,457 B2 | 8/2020 | Lenker et al. | |
| 10,792,061 B2 | 10/2020 | Dewaele et al. | |
| 10,799,223 B2 | 10/2020 | Furlong et al. | |
| 10,874,290 B2 | 12/2020 | Walen et al. | |
| 10,962,093 B2 | 3/2021 | Dewaele et al. | |
| 11,007,026 B2 | 5/2021 | Kowshik | |
| 11,033,255 B2 | 6/2021 | Furlong et al. | |
| 11,051,794 B2 | 7/2021 | Cooper et al. | |
| 11,052,226 B2 | 7/2021 | Salahieh et al. | |

| | | | |
|---|---|---|---|
| 11,103,234 B2 | 8/2021 | Felix et al. | |
| 11,130,244 B2 | 9/2021 | Jogasaki | |
| 11,134,928 B2 | 10/2021 | Felix et al. | |
| 11,141,566 B2 | 10/2021 | Cabiri | |
| 11,241,557 B2 | 2/2022 | Besselink | |
| 11,278,704 B2 | 3/2022 | Pleijers | |
| 11,330,964 B2 | 5/2022 | Thissen | |
| 11,350,914 B2 | 6/2022 | Furlong et al. | |
| 11,382,654 B2 | 7/2022 | Lenker | |
| 11,419,691 B2 | 8/2022 | Kim et al. | |
| 11,457,904 B2 | 10/2022 | Dewaele et al. | |
| 11,523,807 B2 | 12/2022 | Furlong et al. | |
| 11,564,670 B2 | 1/2023 | Furlong et al. | |
| 11,576,735 B2 | 2/2023 | Blanckaert et al. | |
| 11,589,733 B2 | 2/2023 | Sinay et al. | |
| 11,607,242 B2 | 3/2023 | Tada et al. | |
| 11,642,114 B2 | 5/2023 | Thissen | |
| 11,660,101 B2 | 5/2023 | Walen et al. | |
| 11,696,677 B2 | 7/2023 | Thissen | |
| 11,730,921 B2 | 8/2023 | Besselink | |
| 11,730,927 B2 | 8/2023 | Laby et al. | |
| 11,839,401 B2 | 12/2023 | Lenker | |
| 12,048,819 B2 | 7/2024 | Yang et al. | |
| 12,295,550 B2 | 5/2025 | Tilson et al. | |
| 2004/0199052 A1 | 10/2004 | Banik et al. | |
| 2004/0236316 A1 | 11/2004 | Danitz et al. | |
| 2005/0027245 A1 | 2/2005 | Sachdeva et al. | |
| 2005/0273084 A1 | 12/2005 | Hinman et al. | |
| 2005/0273085 A1 | 12/2005 | Hinman et al. | |
| 2006/0199999 A1 | 9/2006 | Ikeda et al. | |
| 2006/0281566 A1 | 12/2006 | Lee | |
| 2007/0049800 A1 | 3/2007 | Boulais | |
| 2007/0250113 A1 | 10/2007 | Hegeman et al. | |
| 2007/0282371 A1 | 12/2007 | Lee et al. | |
| 2007/0287993 A1 | 12/2007 | Hinman et al. | |
| 2008/0249364 A1 | 10/2008 | Korner | |
| 2008/0300462 A1 | 12/2008 | Intoccia et al. | |
| 2009/0069632 A1 | 3/2009 | McIntyre et al. | |
| 2009/0111238 A1 | 4/2009 | Kim | |
| 2009/0124857 A1 | 5/2009 | Viola | |
| 2010/0151161 A1 | 6/2010 | Da Rolo | |
| 2010/0228191 A1 | 9/2010 | Alvarez et al. | |
| 2010/0234831 A1 | 9/2010 | Hinman et al. | |
| 2010/0286480 A1 | 11/2010 | Peine et al. | |
| 2010/0287755 A1 | 11/2010 | Eberhard | |
| 2011/0004157 A1 | 1/2011 | Dewaele et al. | |
| 2011/0295065 A1 | 12/2011 | Gurusamy et al. | |
| 2012/0116163 A1 | 5/2012 | Lutze et al. | |
| 2012/0245414 A1 | 9/2012 | Verbeek | |
| 2012/0277730 A1 | 11/2012 | Salahieh et al. | |
| 2012/0323077 A1 | 12/2012 | Verbeek | |
| 2013/0184528 A1 | 7/2013 | Onuki et al. | |
| 2013/0197490 A1 | 8/2013 | Stanton et al. | |
| 2013/0253469 A1 | 9/2013 | Freed | |
| 2014/0018620 A1 | 1/2014 | Verbeek | |
| 2014/0249474 A1 | 9/2014 | Suon et al. | |
| 2015/0099097 A1 | 4/2015 | Cabiri | |
| 2015/0107396 A1 | 4/2015 | Suehara | |
| 2015/0112134 A1 | 4/2015 | Suehara et al. | |
| 2015/0157353 A1 | 6/2015 | Lenker et al. | |
| 2015/0352728 A1 | 12/2015 | Wang | |
| 2015/0366445 A1* | 12/2015 | Rutgers | A61B 1/2676 |
| | | | 128/200.26 |
| 2016/0015249 A1 | 1/2016 | Suehara | |
| 2016/0096004 A1 | 4/2016 | Gerrans et al. | |
| 2016/0136393 A1 | 5/2016 | Tsai et al. | |
| 2016/0278616 A1 | 9/2016 | Viebach et al. | |
| 2017/0027607 A1 | 2/2017 | Verbeek et al. | |
| 2018/0049873 A1 | 2/2018 | Manash et al. | |
| 2018/0055589 A1 | 3/2018 | Joseph et al. | |
| 2018/0289241 A1 | 10/2018 | Zhou et al. | |
| 2019/0111237 A1 | 4/2019 | Cabiri | |
| 2019/0111238 A1 | 4/2019 | Schultz et al. | |
| 2019/0175869 A1 | 6/2019 | Kirt et al. | |
| 2020/0275983 A1 | 9/2020 | Dewaele et al. | |
| 2020/0330729 A1 | 10/2020 | Petitpierre et al. | |
| 2021/0267702 A1 | 9/2021 | Kim et al. | |
| 2021/0275266 A1 | 9/2021 | Kim et al. | |
| 2021/0378648 A1 | 12/2021 | Thissen et al. | |

(56) References Cited

U.S. PATENT DOCUMENTS

| | | |
|---|---|---|
| 2022/0061634 A1 | 3/2022 | Thissen et al. |
| 2022/0087666 A1 | 3/2022 | Sharma et al. |
| 2022/0117576 A1 | 4/2022 | Mixter et al. |
| 2022/0167836 A1 | 6/2022 | Thissen et al. |
| 2022/0168008 A1 | 6/2022 | Thissen et al. |
| 2022/0331003 A1 | 10/2022 | Cohen et al. |
| 2023/0031313 A1 | 2/2023 | Lynn et al. |
| 2023/0131647 A1 | 4/2023 | Magno et al. |
| 2023/0165573 A1 | 6/2023 | Furlong et al. |
| 2023/0190329 A1 | 6/2023 | Tada et al. |
| 2023/0255644 A1 | 8/2023 | Walen et al. |
| 2024/0138946 A1 | 5/2024 | Swoyer et al. |
| 2024/0173130 A1 | 5/2024 | McNiven et al. |
| 2024/0216008 A1 | 7/2024 | Lenker |
| 2024/0245284 A1 | 7/2024 | Thissen |
| 2024/0306900 A1 | 9/2024 | Thissen et al. |
| 2024/0389835 A1 | 11/2024 | Thissen et al. |
| 2025/0049305 A1 | 2/2025 | Thissen |
| 2025/0049307 A1 | 2/2025 | Thissen |

FOREIGN PATENT DOCUMENTS

| | | | |
|---|---|---|---|
| CN | 101522121 B | 9/2011 | |
| DE | 3219629 A1 | 12/1983 | |
| DE | 4222121 C1 | 9/1993 | |
| DE | 102009037030 A1 | 2/2011 | |
| DE | 102010000787 A1 | 7/2011 | |
| DE | 102010005243 A1 | 7/2011 | |
| DE | 102010000787 B4 | 9/2014 | |
| EP | 0626604 A2 | 11/1994 | |
| EP | 3087944 A1 | 11/2016 | |
| JP | 2008188095 A | 8/2008 | |
| JP | 2009539472 A | 11/2009 | |
| JP | 2009539567 A | 11/2009 | |
| JP | 2012075659 A | 4/2012 | |
| JP | 2015213758 A | 12/2015 | |
| KR | 101312071 B1 | 9/2013 | |
| NL | 2030160 B1 | 6/2023 | |
| WO | 1997042910 A1 | 11/1997 | |
| WO | 2004103430 A2 | 12/2004 | |
| WO | 2006/026520 A2 | 3/2006 | |
| WO | 2008139768 A1 | 11/2008 | |
| WO | 2009/098244 A2 | 8/2009 | |
| WO | 2009/112060 A1 | 9/2009 | |
| WO | 2009/127236 A1 | 10/2009 | |
| WO | 2010/028090 A2 | 3/2010 | |
| WO | 2010105649 A1 | 9/2010 | |
| WO | 2010/136272 A1 | 12/2010 | |
| WO | 2010/136274 A1 | 12/2010 | |
| WO | 2010/151698 A2 | 12/2010 | |
| WO | 2011018147 A1 | 2/2011 | |
| WO | 2011018179 A2 | 2/2011 | |
| WO | 2011079897 A1 | 7/2011 | |
| WO | 2012035531 A1 | 3/2012 | |
| WO | 2012/128618 A1 | 9/2012 | |
| WO | 2012/139869 A2 | 10/2012 | |
| WO | 2012/151396 A2 | 11/2012 | |
| WO | 2012/173478 A1 | 12/2012 | |
| WO | 2013084985 A1 | 6/2013 | |
| WO | 2013173197 A1 | 11/2013 | |
| WO | 2014/011049 A1 | 1/2014 | |
| WO | 2014186736 A1 | 11/2014 | |
| WO | 2015051070 A1 | 4/2015 | |
| WO | 2015/084174 A1 | 6/2015 | |
| WO | 2015085307 A1 | 6/2015 | |
| WO | 2016/030457 A1 | 3/2016 | |
| WO | 2016/061291 A1 | 4/2016 | |
| WO | 2016054063 A1 | 4/2016 | |
| WO | 2016/089202 A1 | 6/2016 | |
| WO | 2016/091856 A1 | 6/2016 | |
| WO | 2016/091858 A1 | 6/2016 | |
| WO | 2016/138443 A2 | 9/2016 | |
| WO | 2016/160694 A1 | 10/2016 | |
| WO | 2016/172706 A1 | 10/2016 | |
| WO | 2017010883 A2 | 1/2017 | |
| WO | 2017014624 A1 | 1/2017 | |
| WO | 2017082720 A1 | 5/2017 | |
| WO | 2017/176766 A1 | 10/2017 | |
| WO | 2017/213491 A1 | 12/2017 | |
| WO | 2018/067004 A1 | 4/2018 | |
| WO | 2018083674 A2 | 5/2018 | |
| WO | 2019/009710 A1 | 1/2019 | |
| WO | 2019077461 A1 | 4/2019 | |
| WO | 2019/096932 A1 | 5/2019 | |
| WO | 2019/096939 A1 | 5/2019 | |
| WO | 2019/139811 A1 | 7/2019 | |
| WO | 2019159142 A1 | 8/2019 | |
| WO | 2020/080938 A2 | 4/2020 | |
| WO | 2020/102389 A1 | 5/2020 | |
| WO | 2020/214027 A2 | 10/2020 | |
| WO | 2020/218921 A2 | 10/2020 | |
| WO | 2020218920 A2 | 10/2020 | |
| WO | 2021/146677 A1 | 7/2021 | |
| WO | 2024033706 A1 | 2/2024 | |
| WO | 2025026670 A1 | 2/2025 | |
| WO | 2025026702 A1 | 2/2025 | |

* cited by examiner

STEERABLE INSTRUMENT COMPRISING A DETACHABLE PART

FIELD OF THE INVENTION

The present invention relates to a steerable instrument for invasive and non-invasive type of applications, such as in surgery. Such instruments can be used in, for instance, the field of gastroscopy, colonoscopy, endoscopy, laparoscopy, and other medical applications. However, the steerable instrument according to the invention can also be used in non-medical applications. Examples of the latter include inspection and/or repair of mechanical and/or electronic hardware at locations that are difficult to reach.

BACKGROUND ART

Transformation of surgical interventions that require large incisions for exposing a target area into minimal invasive surgical interventions, i.e. requiring only natural orifices or small incisions for establishing access to the target area, is a well-known and ongoing process. In performing minimal invasive surgical interventions, an operator such as a physician, requires an access device that is arranged for introducing and guiding invasive instruments into the human or animal body via an access port of that body. In order to reduce scar tissue formation and pain to a human or animal patient, the access port is preferably provided by a single small incision in the skin and underlying tissue. In that respect the possibility to use a natural orifice of the body would even be better. The access device preferably enables the operator to control one or more degrees of freedom that the invasive instruments offer. In this way, the operator can perform required actions at the target area in the human or animal body in an ergonomic and accurate manner.

Steerable surgical invasive instruments in the field of gastroscopy, colonoscopy, endoscopy, laparoscopy, etc. are well-known in the art. The invasive instruments can comprise a steerable tube shaped device that enhances its navigation and steering capabilities. Such a steerable tube shaped device may comprise a proximal end part, a distal end part including at least one deflectable zone, and a rigid or flexible intermediate part or shaft, wherein the steerable tube shaped device, at its proximal end, further comprises a steering arrangement that is adapted to deflect the distal deflectable zone relative to a central axis of the tube shaped device.

Most of the known instruments are complex to manufacture resulting in expensive instruments. Often, the distal end of the instruments comprise a flexible zone that is composed of separate links with hinging pins, coils or flexible plastic extrusions. Steering cables should be guided through holes through these links and/or through guiding eyes or hooks.

In many prior art devices, the steering arrangement comprises conventional steering cables with, for instance, sub 1 mm diameters as control members, wherein the steering cables are arranged between related deflectable zones at the distal end part and the steering arrangements at the proximal end part of the tube shaped device. Alternatively, in any embodiment shown or described herein, control members may be implemented by one or more sets of elongated elements that are, e.g., formed by laser cutting in tube elements. Further details regarding the design and fabrication of the abovementioned steerable tube and the steering arrangement thereof have been described for example in WO 2009/112060 A1, WO 2009/127236 A1, WO 2017/213491 A1, and WO 2018/067004. Such instruments can advantageously be used in endoscopic operations where the length need not be more than say 1 meter. In other embodiments, more specifically instruments which are more than one meter can be made, for example 1-2 meters. They can be configured using elongated elements formed by cutting tube elements and/or by cables or wires.

Sometimes a plastic extruded tube can be used with integrated channels for accommodating the cables. This renders an instrument with a simple construction. However, most plastics are rather weak. In case of very long instruments, e.g. longer than 1 meter, problems may arise due to the high forces exerted on the cables, both the steering cables and the actuation cable arranged to operate the tool at the distal end of the instrument. Problems may be undesired cuts, slip stick effects in the plastic tube and often too high friction on the cables causing steering by the steering cables to be difficult and hard to manage. Moreover, mechanical properties of many plastics may be too poor to guarantee a high enough torsional stiffness which is required because the instruments should be capable of being rotated in use where they may have been guided through several curves impeding rotation of the whole instrument. Another disadvantage of a plastic tube may be that in case it is provided with an actuation cable to operate a tool at the distal end of the instrument the force in the actuation cable can increase to an extent that it exceeds the maximum longitudinal force allowed in the extruded plastic tube. If so, it would be impossible to operate the tool with an acceptable force. Moreover, if the plastic tube is in a curved arrangement and high force is exerted on the actuation cable, the channels for the steering cables may be deformed, especially in bent/deflected portions, such that the steering cables are clamped and cannot move freely anymore in the channels, thus, impeding proper operation of the steering of the distal deflectable zones.

In medical applications where longer instruments are necessary, such as in colonoscopy where 1.5 meter long instruments (or longer) may be applied, requirements as to steerability, flexibility, stiffness and accuracy increase seriously. There is a desire to develop such instruments with a better performance than prior art devices as to steerability also under end-effector actuation, longitudinal stiffness, torsion stiffness, durability and applicability of a mechanically actuated tool at the distal end.

In medical applications, contamination of an instrument after it has been used to perform a surgical procedure on a patient can be a problem resulting in undesired post-operative complications. The contamination may be due to blood, other body fluids, tissue, etc. As a consequence of the contamination, the instrument may contain germs, viruses or other biological or chemical substances that could threat the health of the next patient on which the instrument is used.

One way of avoiding this contamination requires performing a thorough cleaning and sterilization of the instrument before each use. In many cases, the cleaning process is not capable of removing all contamination, and/or is very expensive. Therefore, a risk of adverse effects on a patient that is treated with such an instrument still exists. In order to prevent the risk of contamination, there is a preference for using disposable instruments which are used a single time and are thrown away after treating one patient.

SUMMARY

According to a first aspect of the invention, a steering device for connecting to an elongated instrument comprises a locking plate with a coupling to which a steering plate of the instrument can secure such that the steering plate and the locking plate move together; and a steering unit for moving the locking plate. The elongated instrument comprises a plurality of elongated elements extending along an instrument shaft and secured to a steering plate at a proximal end of the instrument shaft, with the steering plate being movably connected around a support member secured to the shaft.

Such a steering device can allow for easy coupling and decoupling of an instrument for medical or other operations. The elongated instrument can use the elongated elements for steering purposes, allowing for bending and movement at a distal end in any number of directions controlled by the steering unit. By having a steering plate to which the elongated elements secure, the elongated elements are held in tension for proper steering, and the steering plate allows for easy connection and disconnection. This allows for the instrument to be quickly, securely and easily coupled to a steering unit when needed, by even non-technical persons. With this simple connection, the instrument could be disposable while more complicated steering device and steering unit parts are reusable.

According to an embodiment, the locking plate comprises a first plate with one or more openings for receiving one or more protrusions from the steering plate; and a second plate which can secure the one or more protrusions in the one or more openings. Optionally, the second plate rotates from an open position to allow movement of the one or more protrusions into or out of the one or more openings, to a locked position where the steering plate is secured to the locking plate and the one or more protrusions cannot move out of the one or more openings. Such a connection allows for quick, secure and easy coupling and decoupling of the instrument to the steering device. While an opening and protrusion coupling are shown and discussed, many other kinds of quick and secure couplings could be used, for example, using snaps, clamps, magnets, etc.

According to an embodiment, the steering unit comprises one or more frames connected around one or more axes to enable movement of the steering plate in space. By enabling any movement of steering plate, the movement of the instrument can be more precisely controlled.

According to an embodiment, the locking plate connects to the steering unit such that the locking plate can rotate in relation to the steering unit. Optionally, the locking plate connects to the steering unit with a circumferential ball bearing. Such a connection can allow rotation of the instrument as well as bending movements at the distal end.

According to an embodiment, the elongated elements are flexible cables or wires extending through the instrument for moving a distal end of the instrument. In other embodiments, the elongated elements could be rigid cables or wires, thereby enabling pushing and pulling movements by the steering device for controlling the movement of instrument very precisely.

According to a further aspect of the invention, an elongated instrument for connecting to a steering device comprises an elongated shaft with a distal end and a proximal end; a steering plate located at the proximal end of the shaft, the steering plate movably arranged around a central supporting member connected around the shaft, the steering plate comprising a coupling for coupling the steering plate to a steering device for controlling movement of the steering plate; and a plurality of elongated elements extending along the shaft and secured to the steering plate at the proximal end.

Such an instrument can be used in a variety of medical operations, with the elongated elements and steering plate allowing for bending and controlled movement of the instrument during operations in any number of directions. The steering plate allows for precise control of the degree and direction of bending or movement, and can easily and quickly connect to (and disconnect from) a variety of manual or robotic steering devices. The instrument is ready for use with a simple coupling, and then can be disposed of after a simple decoupling, leaving most complicated (and expensive) parts; e.g., steering, handle, robotics parts; for reuse with a new instruments. In some embodiments, the removal of the instrument from the steering device can allow for easier decontamination for reuse instead of disposal.

According to an embodiment, the plurality of elongated elements are secured circumferentially around the steering plate. This allows for bending in any number of directions (depending on number of and placement of elongated elements) of the instrument's distal end, or any portion of instrument shaft to which the elongated elements are connected.

According to an embodiment, the coupling comprises one or more elements for releasably connecting to a locking plate of the steering device. Optionally, the one or more elements comprises one or more extensions which can releasably secure to the locking plate of the steering device. The coupling could also come in different forms, for example, the steering plate having openings and the locking plate having extensions, coupling with snaps, clamps, etc., but must provide a secure coupling which can be quickly and easily used for securing an instrument to a steering device and decoupling when desired.

According to an embodiment, the central supporting member comprises a ball-shaped element and the steering plate is connected to the ball-shaped element such that the steering plate can rotate around the ball shaped element. Such a ball-shaped element can allow for the movement steering plate needs with respect to the instrument shaft while preventing any movements which could cause twisting or tangling of the elongated steering elements.

According to an embodiment, the plurality of elongated elements extend through a plurality of openings in the steering plate and each elongated element comprises a catch at the proximal end to secure the elongated element to the steering plate. Optionally, the plurality of elongated elements comprises a plurality of flexible wires or cables. Further optionally, the plurality of flexible wires or cables are tensioned between a position along the shaft and the steering plate. Such an arrangement can ensure that the elongated elements stay tensioned to the extent needed for precise steering control. This is particularly important when using flexible cables or wires. The connections and tensioning can be done when the instrument is being manufactured, such that only a simple coupling to a steering unit needs to be done before using the instrument for an operation. In a further embodiment, the coupling could be designed to tension the elongated elements or ensure proper tensioning.

According to a further aspect of the invention, a method of manufacturing a steerable instrument which can be coupled to a steering unit comprises forming an instrument with an elongated shaft and a steerable portion; movably connecting a steering plate around the shaft at a proximal end, the steering plate comprising a coupling for coupling the steering plate to a steering device for controlling movement of the steering plate; and connecting a plurality of elongated instruments to the steerable portion and to the steering plate. Such a method can manufacture a steerable instrument which can connect or disconnect quickly and easily from a steering device to perform operations.

According to an embodiment, the step of connecting a plurality of elongated elements to the steerable portion and to the steering plate comprises connecting a plurality of elongated elements to a support part comprising a plurality of fingers, each of the plurality of elongated elements connecting to one of the plurality of fingers; and connecting the plurality of elements with the support part to the steerable portion and to the steering plate. Using a support part with a plurality of fingers can ensure the elongated elements are supported and in proper position to easily connect to a steering device. Such a configuration could enable the steering plate to be part of the reusable steering device and not part of the disposable instrument, resulting in less waste and costs for the disposable portion of the instrument.

According to a further aspect of the invention, an elongated instrument for connecting to a steering device comprises an elongated shaft with a distal end and a proximal end; a support part at a proximal end of the shaft, the support part comprising a base portion and a plurality of fingers extending circumferentially outward from the longitudinal axis; and a plurality of elongated elements extending along the shaft and secured to the support part at the proximal end. Such a support part ensures that the elongated elements of the instrument are properly positioned for connecting to the steering device for easy coupling and decoupling. The support part can also ensure that the elongated elements are held in tension for proper storage of the instrument and to ensure that the elements work as intended for controlling movement of the instrument distal end in use. The support part can be formed of metals, plastic or a combination of materials depending on the configuration.

According to an embodiment, the base portion connects around the shaft. This can be through a tight coupling, welding, bonding, adhesive, screws, screwthread, spring elements, or any other means that will secure the base portion with respect to the shaft. The base portion may extend only a short distance near the proximal end of the instrument, or in some embodiments it may extend through the length or substantially the whole length of the shaft to the distal end. The base portion ensures a stable support from which the fingers extend for positioning and securing the elongated elements properly.

According to an embodiment, the base portion comprises an elongated tube, with the fingers formed by cutting the elongated tube into a plurality of longitudinal sections. Optionally, the cuts could extend throughout the elongated tube to at least partially transmit bending forces from a proximal end of the instrument to the distal end of the elongated instrument, thereby helping in steering the distal end of the instrument. The elongated tube can be an outer tube, or could be surrounded by one or more further tubes and/or protective layers. The use of an elongated tube being cut to form fingers provides a simple way to form the support part and ensure that base portion and fingers do not separate. Additionally, the forming of fingers from a tube used for steering could ensure that the elongated elements are configured for easy coupling without adding additional diameter or parts to the instrument.

According to an embodiment, each of the fingers comprises a collar and/or opening to which an elongated element secures. The collar could be, for example, a body connected on a radially inside of a finger with a channel for receiving and securing an elongated element and/or a connection member of an elongated element. The opening could be any shaped opening (e.g., hole, keyhole) in the finger which could receive and secure an elongated element and/or a connection member of an elongated element. Thus, elongated elements are secured to fingers for proper configuration to easily couple to a steering device and to ensure they do not become uncoupled prior to or during use. Elongated elements are coupled such that they will be able to move longitudinally during use of the instrument. In some embodiments, the elongated element could be tensioned by the connection to the collar or opening. This can further ensure that elongated elements are properly positioned and ready for use when needed. The tensioning can be through a frictional connection, or through a bonded or mechanical attachment or connection. If through a bonded or mechanical attachment, the attachment could be configured to break upon connection to a steering device and/or use, thus facilitating the longitudinal movement of elongated elements for proper steering.

According to an embodiment, the plurality of fingers of the support part can move from a storage position where the fingers extend close to the longitudinal axis of the instrument to a use position where the fingers extend outward from the axis. Such a configuration can allow for a smaller envelope for transport and storage, while allowing for easy movement into a use configuration. The ability to move the fingers closer to the longitudinal axis also can allow for the use of less packaging materials due to the overall smaller volume.

According to an embodiment, the fingers could be biased outwardly to the use position when resting, ensuring that the support part and instrument are ready for coupling as soon as packaging or other material is removed.

According to an embodiment, the support part and/or the elongate instrument comprise a coupling part for coupling to a steering device. This can be in the shaft and/or elongated elements, for example, coupling parts on the ends of elongated elements and/or portions of fingers can secure to parts of the steering device. In some embodiments, the elongated elements and/or fingers connect to a steering plate, and the shaft connects to the steering device as well. The steering device can then move the elongated elements longitudinally with respect to the shaft thereby controlling the distal end movements of the instrument.

According to an embodiment, the elongated elements are flexible wires or cables. The support part is especially useful with the flexible wires or cable, as the support part can ensure they are positioned for easy and proper coupling with a steering device despite the flexibility of the individual wires or cables. Optionally, the support part can even tension the wires or cables helping to ensure they transmit proper forces for control of the distal end, or the part of the instrument to which they are secured.

Further features and advantages of the invention will become apparent from the description of the invention by way of non-limiting and non-exclusive embodiments. These embodiments are not to be construed as limiting the scope of protection. The person skilled in the art will realize that other alternatives and equivalent embodiments of the invention can be conceived and reduced to practice without departing from the scope of the present invention. Moreover, separate features of different embodiments can be combined, even if not explicitly shown in the drawings or explained in the specification, unless such combination is physically impossible. The scope of the present invention is only limited by the claims and their technical equivalents.

BRIEF DESCRIPTION OF THE DRAWINGS

The present invention will be discussed in more detail below, with reference to the attached drawings, in which like or same reference symbols denote like, same or corresponding parts, and in which.

DESCRIPTION OF EMBODIMENTS

Similar reference numbers will be used in different figures for indicating similar elements.

Figures 1A, 1B:
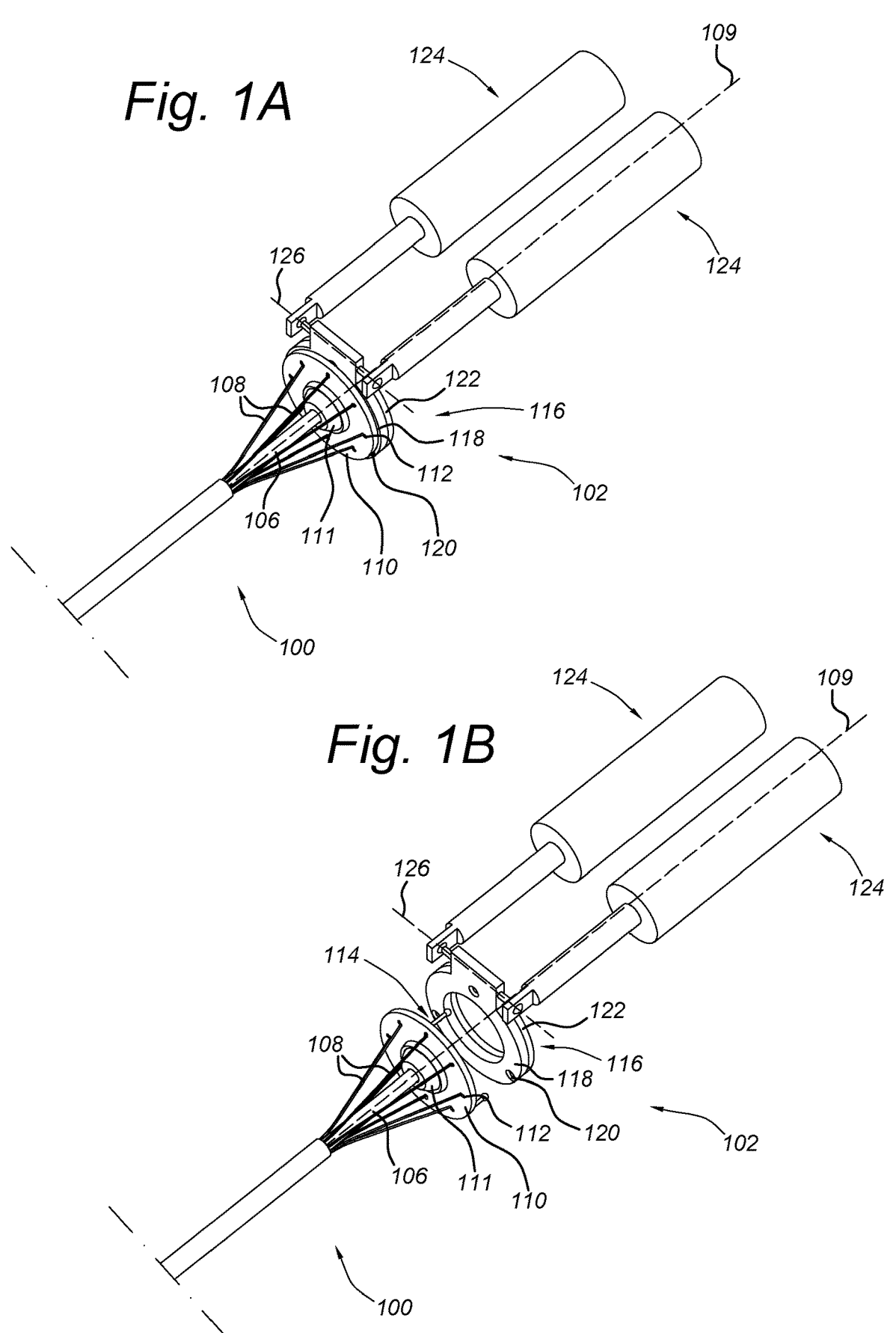
FIG. 1A shows an instrument with steering device according to an embodiment of the invention.
FIG. 1B shows an instrument with steering device of FIG. 1A, with the instrument disconnected from the steering device.
Figure 2A:
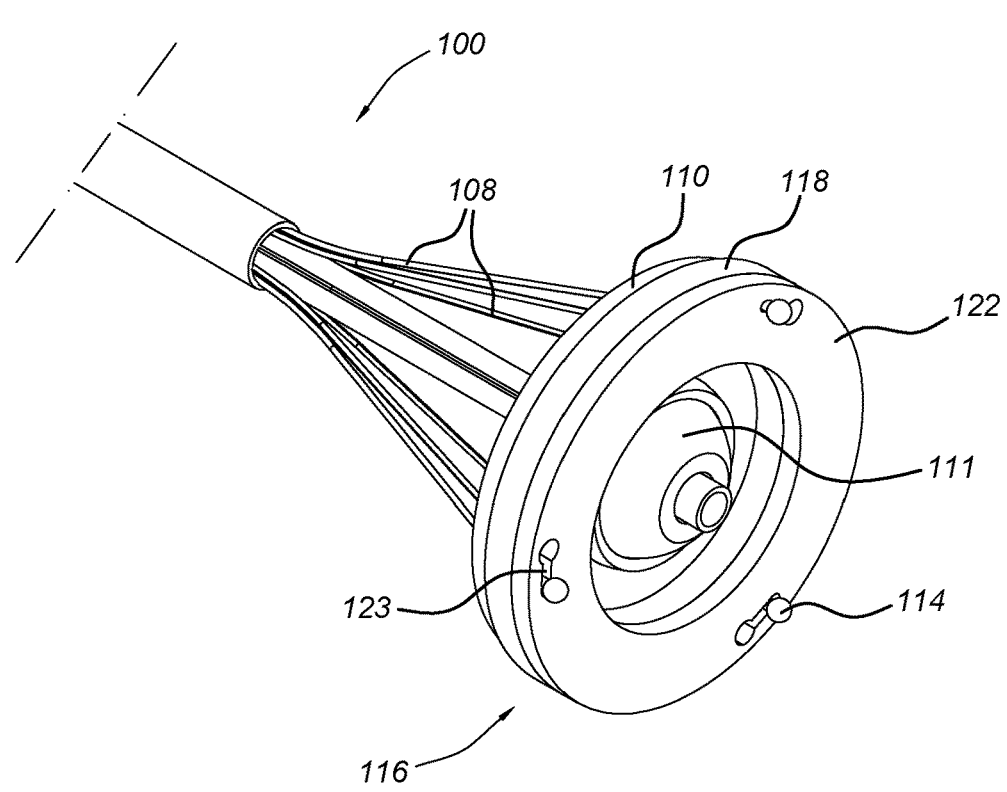
FIG. 2A shows a perspective view of an end of an instrument and a locking plate of a steering device.
Figure 2B:
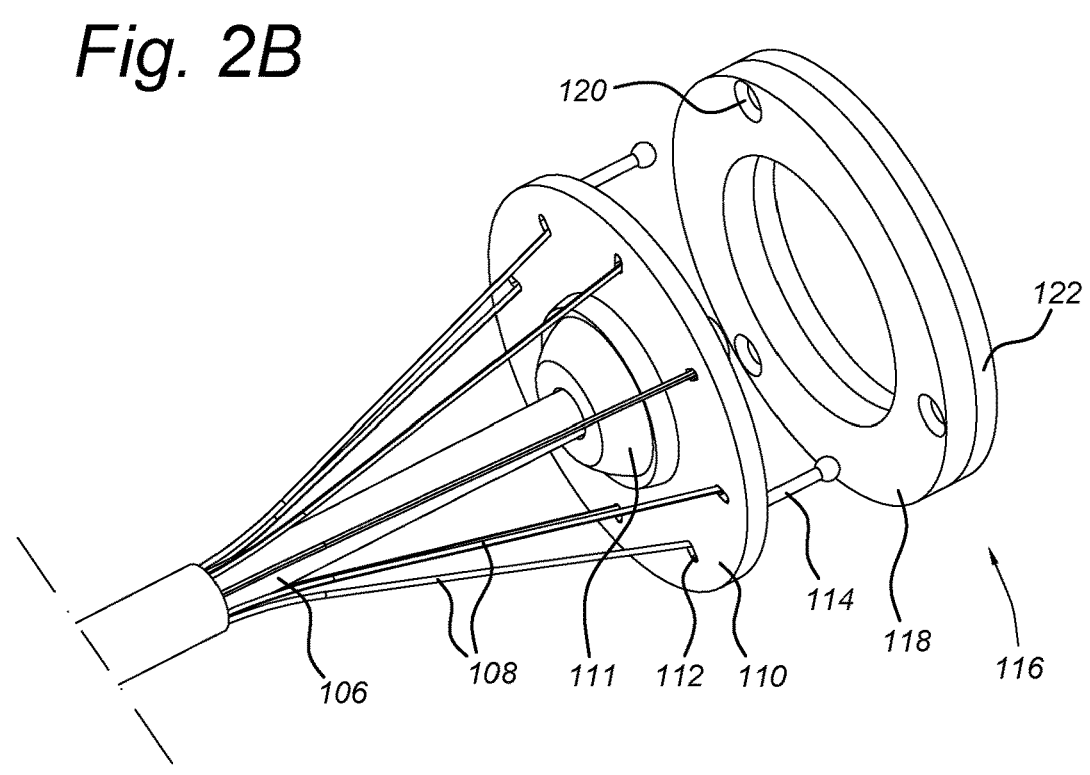
FIG. 2B shows a perspective view of the end of the instrument and locking plate of FIG. 2A, with the instrument separating from the locking plate.

FIG. 1A shows a non-limiting embodiment of an instrument 100 with steering device 102 according to an embodiment of the invention. FIG. 1B shows the instrument 100 disconnected from the steering device 102. FIG. 2A shows a close-up perspective view of an end of instrument 100 and a locking plate 116 of steering device 102 secured together, and FIG. 2B shows a perspective view of the end of the instrument 100 and locking plate 116 decoupled.

Instrument 100 is shown schematically to represent any steerable instrument for use in medical or other operations. Suitable instrument arrangements can be found in NL2021823, titled Steerable instrument comprising a tube element, Filed on Oct. 16, 2018 and hereby incorporated by reference. Instrument 100 comprises an elongated shaft 106 and a plurality of elongated elements 108 arranged around a central axis 109. The elongated elements 108 shown are flexible cables or wires, which extend along instrument shaft 106 and connect to steering plate 110 at a proximal end of the instrument and to a distal deflectable section at a distal end of the instrument (not shown). Alternatively, such elongated elements may be implemented by longitudinal strip shaped elements in tube elements and separated by longitudinal slots resulting from laser cutting predetermined patterns in the cylindrical tubes, as explained in detail in for example WO 2009/112060 A1, WO 2009/127236 A1, WO 2017/213491 A1, and WO 2018/067004, or by rigid cables or wires.

The steerable instrument can include a handle arranged at the proximal end if manually operated (see FIGS. 10A-10D) for steering the distal end of the instrument and/or for manipulating a tool, arranged at the distal end of the instrument. Such a tool can, for example, be a camera, a manual manipulator, e.g. a pair of scissors, manipulators using an energy source, e.g. an electrical, ultrasonic or optical energy source. The instrument has no limitation as to the type of tool applied at the distal end. The type of handle or robotic steering unit and/or connection will be selected depending on the type of tool applied at the distal end, the intended use and other instrument or operational requirements.

Steering plate 110 of instrument 100 movably connects to support member 111, which is shown in this embodiment as ball-shaped, though could be shaped differently in different embodiments. In some embodiments steering plate 110 may be connected differently (e.g., directly to channel or locking plate) and/or not include a support member 111. Support member 111 is rigidly connected around shaft 106 at a proximal end of shaft 106. Steering plate 110 can deflect (but not rotate) around support member 111. This can be done, for example, with a pin and recess in support member 111 and steering plate 110, respectively. Such movement enables steering plate 110 to move for steering operations but prevents full rotation which could result in winding elongated elements 108, which could result in loss of steering capabilities and less control of the deflection of distal end of instrument 100.

Each elongated element 108 connects through an opening 112 in steering plate 110 and secures to steering plate 110 in one of a variety of different ways, for example, crimping, bending an end of the element, attaching a ball or other device larger than the opening to an end of the element, etc. Elongated elements 108 connect to different portions of steering plate 110, typically circumferentially around steering plate 110. While the connection of elongated elements 108 to steering plate 110 is depicted as open; in an instrument for use, elements 108 and possibly steering plate 110 would likely be covered, e.g., by a sleeve. The securing of elongated elements 108 to steering plate 110 is typically done at manufacture, such that instrument 100 can be shipped to a location ready for use by a simple coupling to a steering device 102. Different instruments can include different numbers of elongated elements 108 depending on the deflection capabilities desired.

Connected to steering plate 110 are three axially extending protrusions 114 for connecting instrument 100 to locking plate 116 of steering device 102. Different embodiments could have more or fewer connection points and/or could include a different releasable coupling arrangement for connecting instrument 100 with steering plate 110 to steering device 102.

Steering device 102 includes locking plate 116 with first plate 118 with openings 120 and second plate 122 with securing slots 123 (see FIG. 2A) such as to make bayonet fittings. First plate 118 is rotatably connected to second plate 122 such that second plate 122 can be in an open position where a wider portion of securing slot 123 is aligned with openings 120 to a closed position (see FIG. 2A) where a narrow portion of securing slot is aligned with openings 120. In the closed position, protrusions 114 are secured in openings 120 and steering plate 110 is thereby secured to locking plate 116 to move with locking plate 116.

Locking plate 116 is connected to steering unit 102. A simple version of a steering unit 102 and connection is depicted in FIGS. 1A-1B, with locking plate 116 connected to actuators 124 around a hinge axis 126. Other embodiments could include another frame, with another hinge axis (See, e.g., FIGS. 3A-3B) to enable any movement of steering plate 110 (as well as locking plate 116) in space. Steering unit 102 could be controlled manually, or through robotics, or a combination of the two.

As depicted in FIGS. 1A and 2A, instrument 100 connects to steering device 102 through steering plate 110 connecting to locking plate 116 by securing protrusions 114 in openings 120. Second plate 122 is rotated such that protrusions are secured by slots 123 and cannot go back through openings 120.

Instrument 100 can then be controlled by steering device using actuators 124 to move locking plate 116. As steering plate 110 is secured to locking plate 116, steering plate 110 will be moved with locking plate 116 movement around support member 111, causing tension in some elements 108 and relaxation in other elements 108. This will cause an angular deflection out of the axis 109 of instrument shaft 106 in a distal end of instrument 100 to which elements 108 are also connected (as shown in FIG. 3B). Elements 108 could, in some embodiments, be connected at a point along instrument 100 shaft 106 (not at the very distal end), causing bending or deflection in the part of instrument shaft 106 to which element 108 is connected. Any number of deflection or bending zones can be included by using an appropriate number of elongated elements 108 and connecting them at appropriate positions along the length of instrument 100. Additionally, the amount of angular deflection can be reduced from the proximal end to the distal end be connecting the elements at the proximal end at points a greater radial distance around the longitudinal axis than at the distal end. This results in larger movements at the proximal end translating into smaller deflections at the distal end to ensure precise and accurate movements of the tool at the distal end. The instrument could in some embodiments be configured in the opposite manner where movement from the proximal end were amplified at the distal end.

When the operation or procedure is completed, instrument 100 can be easily and quickly disconnected from steering device 102. This is done by rotating second plate 122 to an open position and moving instrument 100 and thereby steering plate 110 and protrusions 114 axially away from steering unit 102 and out of openings 120. Instrument 100 can then be discarded, with steering device 102 available to use with a new, clean instrument 100 for further operations. In some embodiments, instrument 100 could be sent for cleaning and sanitization for preparing for reuse. In such embodiments, the ability to disconnect the part needing cleaning can help to ensure proper cleaning and sterilization can be done. For example, a disconnected instrument could be placed in a sanitization chamber, whereas an instrument which didn't disconnect may not be due to size and/or other sensitive parts.

As discussed in the background, past instruments that were reused needed to go through extensive cleaning and decontamination operations for safe reuse. This was a time consuming process that did not always eliminate all contaminants. Some steerable instruments were disposable to avoid the time, costs and risks of attempting cleaning, but disposing of a full instrument after every operation is quite costly. By using a steering device 102 which can couple to and decouple from an instrument 100 in a quick, easy and secure manner, only the part of the instrument which experiences the contamination can be disposed of (or cleaned and sterilized in some situations), and other parts can be safely reused without the need for extensive decontamination processes. As steering portions of such instruments can be complicated and a relatively expensive part, being able to decouple the exposed portion of the instrument from the steering portion, and only disposing of the exposed portion is a great economic benefit and results in less waste. Using a quick and simple coupling between steering plate 110 and locking plate 116 of steering device 102 allows for quick coupling and decoupling of a disposable instrument 100 to a reusable steering device 102 at the location of use, and by non-trained or non-technical persons.

Figure 3A:
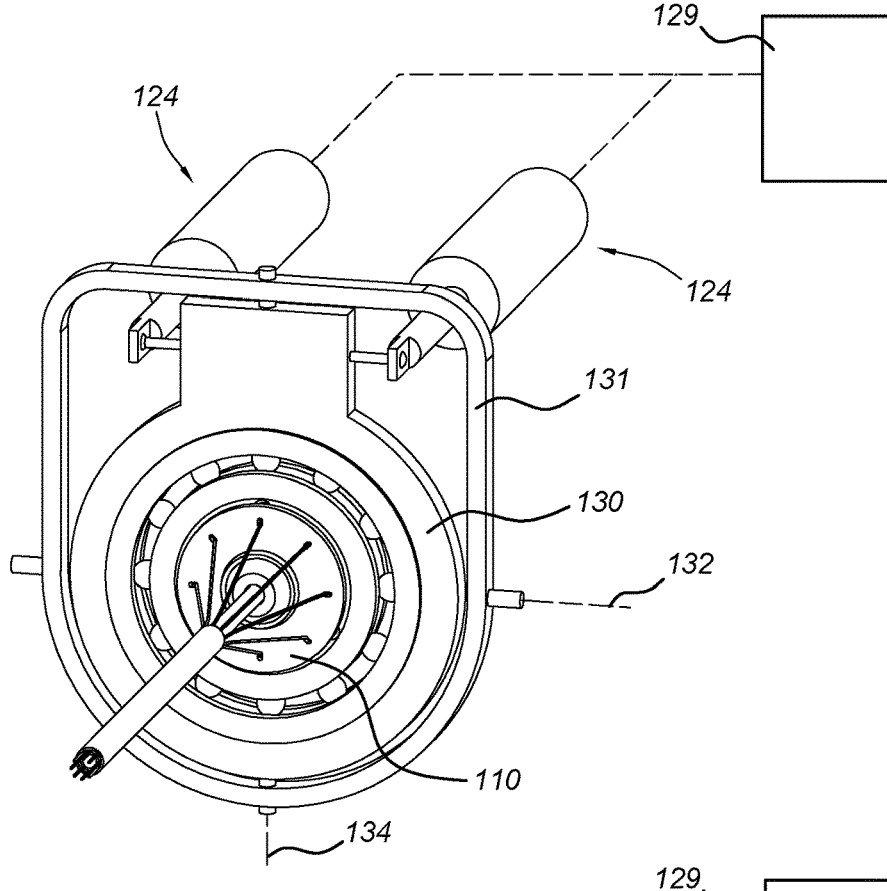
FIG. 3A shows a perspective view of an embodiment of an end of an instrument connected to a steering device.
Figure 3B:
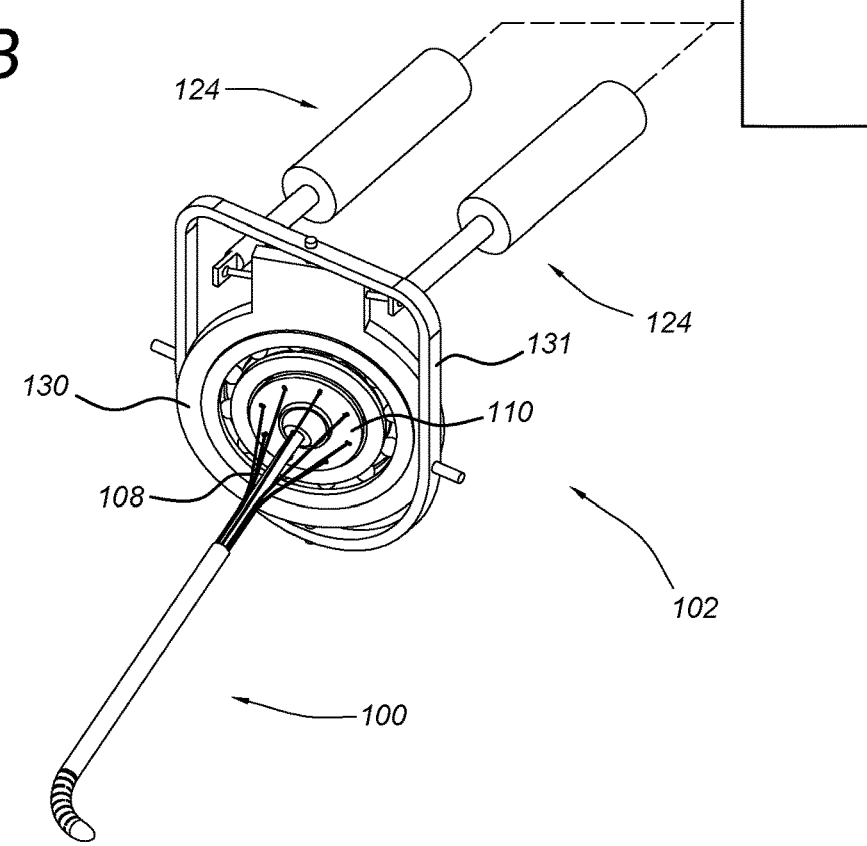
FIG. 3B shows the full instrument with steering device, connected and with a deflection of the distal end.

FIG. 3A shows a perspective view of a second embodiment of an end of an instrument 100 connected to a steering device 102 which includes a schematic depiction of robotic control 129, and FIG. 3B shows the full instrument 100 with steering device 102, connected and with a deflection of the distal end. Instrument 100 is coupled to steering device 102 as in FIGS. 1A-2B, with steering plate 110 coupled to a locking plate of steering device 102 (not shown in FIGS. 3A-3B).

Steering device 102 includes inner frame 130 connected to outer frame 131 at hinge axis 134 such that inner frame 130 can rotate within outer frame 131 about axes 134. The rotation about axis 134 is controlled by actuators 124. Outer frame 131 is connected to steering device 102 at hinge axis 132 (such a connection is not shown in FIGS. 3A, 3B). The rotation about axis 132 is also controlled by actuators 124. Such a suspension about two axes 132 and 134 allows movement of steering plate 110 at any angular position in space. Steering plate 110 is also circumferentially coupled to inner frame 130 with a ball bearing suspension such that the steering plate 110 and therefore instrument 100 can be rotated within inner frame 130. This rotational suspension can be a rotational bearing between locking plate 110 and inner frame 130, though could be done in other manners in different embodiments. The rotation rotates locking plate 110 (therefore rotating elements 108) and all of instrument, including instrument shaft 106. Generally, shaft 106 (or another tube of instrument 100) is configured to ensure that the instrument stays in the desired deflected position, therefore ensuring rotation is along the longitudinal axis and not resulting in orbital rotation of the deflected tip. This ensures that cables 108 do not become twisted from rotational movements and the tip can rotate while keeping its spatial orientation.

FIG. 3B shows an example of a deflection of steering plate 110, causing a deflection in a distal end of instrument 100. Actuators 124 move inner frame 130 such that it is deflected in a certain direction. This causes tension in some wires and relaxation in others, thereby causing the deflection at the distal end. For a different deflection, steering mechanism 102 could cause rotation of frame 131 around axis 132. Instrument 100 could also be rotated in this bent position by causing steering plate 110 to rotate with respect to inner frame 130. This rotation is translated to the distal end through rotation of the shaft, inner and/or outer tubes along instrument 100. The distal end (with possible tool) of instrument 100 is then rotated. Some embodiments could include the wires connected differently at the distal end (e.g., rotated 180 degrees) such that they cause opposite deflection of the distal end for the same movement depicted in steering unit 102. As discussed above in relation to FIGS. 1A-1B, deflection movements could be increased or decreased.

As can be seen in FIGS. 3A-3B, in order to enable movement in any three dimensional plane as well as rotational movement of steering plate 110, and therefore any bending or rotation of instrument 100, the suspension and control through steering device 122 can be complicated. By using a steering plate 110 to which elongated elements 108 of instrument secure, and providing a quick but simple and secure coupling to a locking plate 116, steering device 102 can be reused while allowing for a disposable instrument 100. This enables more complicated steering devices 102, particularly useful in robotics applications.

FIGS. 1A-3B show an instrument which uses flexible wires or cables for elongated elements 108 for the steering of the instrument. Such an instrument requires a connection of elongated elements 108 to steering plate 110 which connects to shaft 106 (through support member 111) or another fixed connection at proximal end to ensure elongated elements 108 are held in tension to enable proper steering movements when connected to steering device 102. Such tensioning can be done at manufacture and/or could be partially done through the coupling used for coupling to steering device 102 (e.g., see FIGS. 10A-10D). The movements of steering device 102 causing steering plate 110 to move result in movement of instrument, particularly bending at distal tip. Then frames 130, 131 are aligned as shown in FIG. 3A, elongated elements 108 are in the rest position and instrument generally extends straight along its longitudinal axis (or whatever rest position instrument is configured for). When steering device 102 causes movement of one of the frames, for example, bending around axis 132, elongated elements on one side of axis 132 are pulled in tension, and elongated elements on the opposite side move to a position of relaxation. This results in bending of distal tip in 3D space as the tensioned elongated elements pull the distal top of instrument 100 in that direction with the relaxed elements allowing the bending movement. Of course, more complicated bending and/or rotational movements can be performed through the use of frames and axes of rotation, particularly when a robotic steering device 129 is used to control precise movements.

FIGS. 4-10D show alternative embodiments which could use cables, wires or other elongated elements with rigidity in the longitudinal direction (the Figures show elongated strips as a schematic depiction only). Instruments using such rigid cables or wires 108 would have additional deflection capability in that elements 108 could be pushed or pulled by steering plate 110 for precise deflection of distal tip of instrument 100. Additionally, the longitudinal rigidity of rigid cables or wires could eliminate the need for steering plate 110 to connect to shaft 106, as the rigid elongated elements would not need to be tensioned to steering plate 110. Therefore, they could be connected to a steering/locking plate directly, as shown in the following embodiments.

Figures 4, 5:
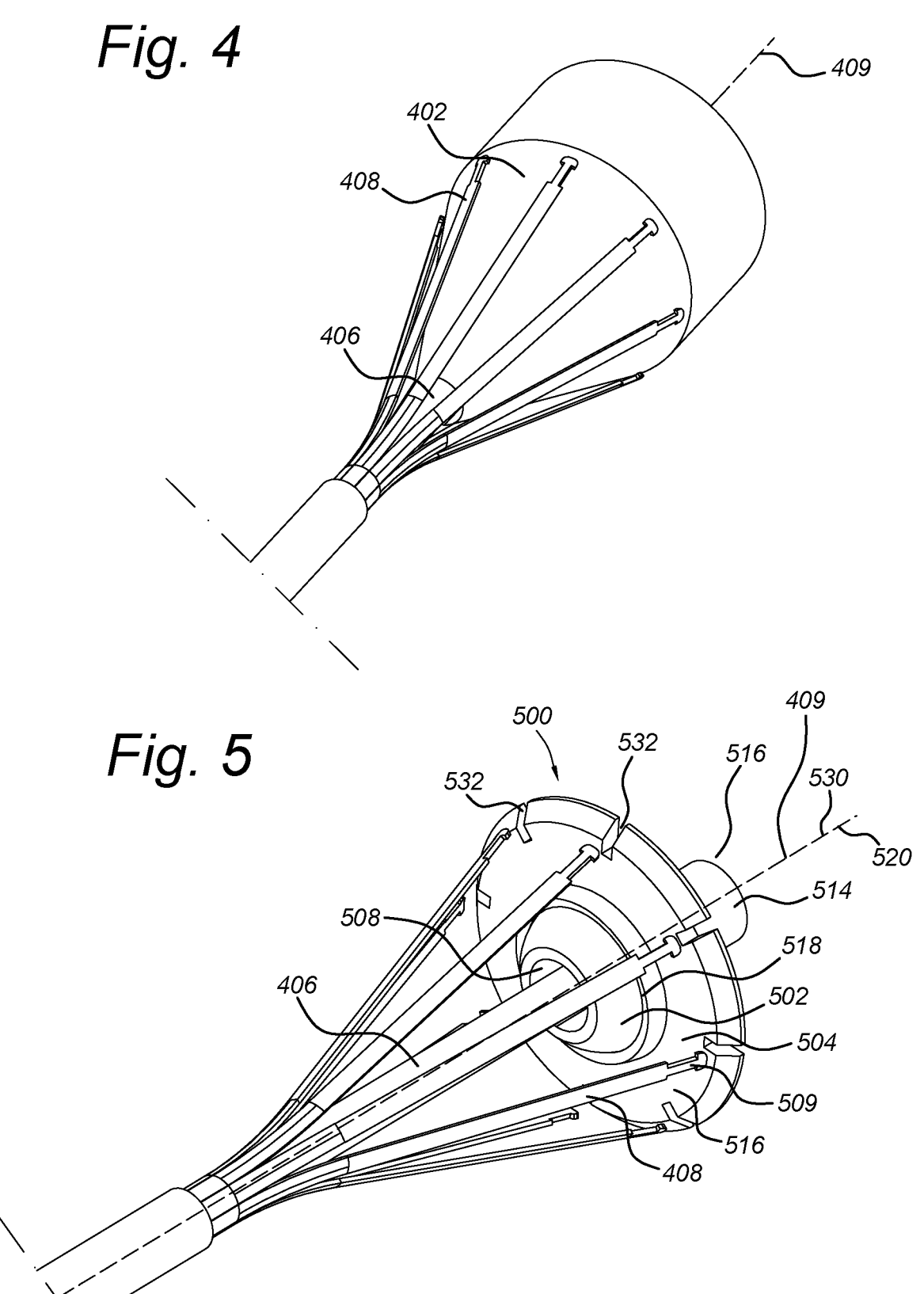
FIG. 4 shows perspective view of rigid elongated elements being expanded for connection to a steering plate.
FIGS. 5-7 show rigid elongated elements connecting to different embodiments of a steering plate.

FIG. 4 shows an example of expanding rigid elongated elements 408 to connect to a steering plate that is part of steering unit (instead of part of the disposable instrument as seen in FIGS. 1A-3). Elongated elements 408 are arranged to extend outwardly from the central axis 409 of the instrument by a cone-shaped device 402, wherein the cone-shaped device 402 is arranged surrounding shaft 406 such that the elongated elements 408 are expanded by the outer surface of the cone-shaped device 402.

It should be understood that any other suitable device or method can be used to suitably arrange the elongated elements at the proximal end such that the elongated elements extend outwardly from the central axis of the instrument.

FIG. 5 shows a steering device 500 according to one embodiment with an instrument being connected.

The steering device 500 comprises a supporting member 502 and a steering member 504. The supporting member 502 comprises a ball-shaped element traversed by a first channel 508 wherein the first channel 508 has a circular shape and extends from a proximal end 510 of the steering device 500 to a distal end 512 of the steering device 500. The first channel 508 extends from the ball-shaped element 506 at the proximal end of the steering device 500 thereby defining a hollow tube 514 which extends outwardly from the ball-shaped element.

The steering member 504 comprises a steering plate 516 and a second channel 518 located at the centre of the steering plate 516 wherein the second channel 518 comprises a circular shape. The supporting member 502 is arranged in the second channel 518 such that the steering member 504 can move around the ball-shaped element 506 (but not rotate about central axis 530 as explained in relation to FIGS. 1A-2B), and such that the central axis 520 of the first channel 508 coincides with the central axis 530 of the second channel.

The steering plate 516 comprises a plurality of grooves 532 extending inward from the circumference of the steering plate 516 wherein the grooves 532 have a U-shape, though could take a number of different shapes in different embodiments.

The steering device 500 is arranged to be attached to the instrument in the following way. Each elongated element 408 includes a connecting part 509 which can fit into groove 532 and secure in groove 532. In this case, a T-shaped connection is formed with a narrower portion to go within the groove and a wider portion at the end to ensure no longitudinal movement of elongated elements is allowed once connected. The inner shaft 406 of the instrument is introduced into the side of the first channel 508 of the supporting member 502 located at the distal end of the steering device 500 such that the central axis 409 of the instrument coincides with the central axis 520 of the first channel 508 and such that the connecting part 509 of the elongated elements 408 align with the grooves 532. The connecting part 509 of the elongated elements 408 is then pushed into the grooves 532 such that the upper wider part of the T shape is secured at a proximal side of the steering plate, as shown in FIG. 6.

Once elongated elements 408 are secured to steering plate 516, movement of steering plate 516 around the support element 506 pushes or pulls the elongated elements 408 thereby causing distal deflection (as seen in FIG. 3B).

Figure 7:
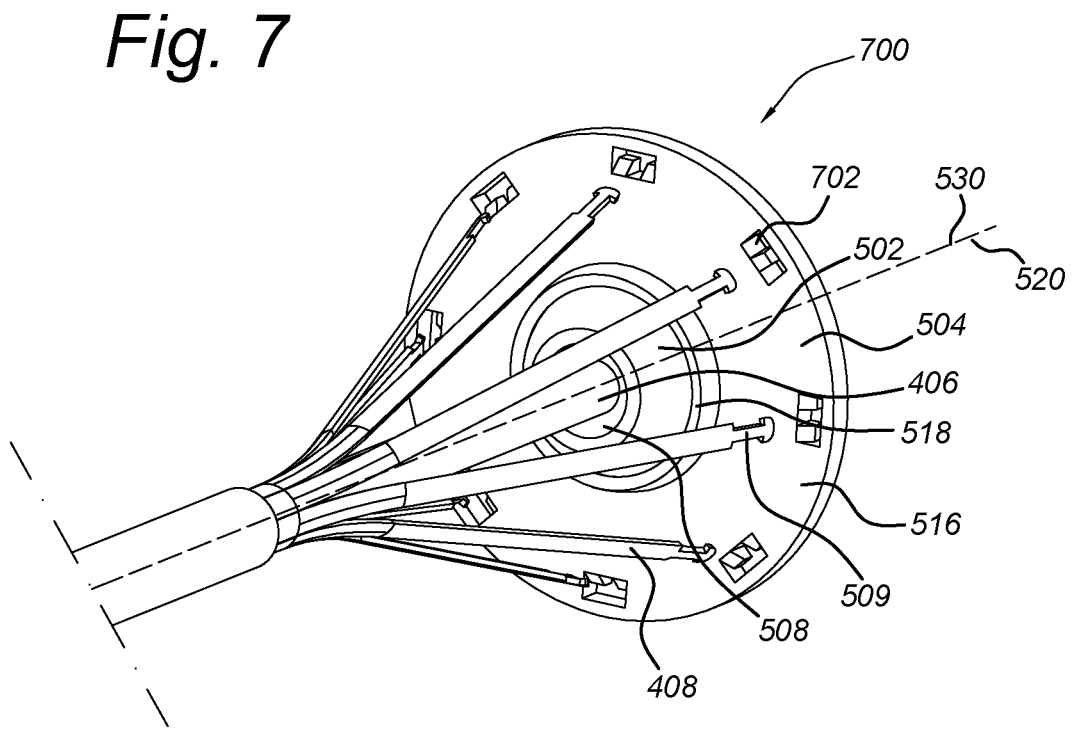

FIG. 7 shows an alternative embodiment of the steering device 500 of FIG. 5 wherein the steering plate 516 comprises a plurality of openings 702 instead of circumferential grooves. The way of attaching the instrument to the steering device 700 is similar to that explained with reference to FIG. 5 but in this embodiment the connecting parts 509 of the elongated elements are pushed against the openings, such that they "click" into a receiving portion of the steering plate 516. As can be seen in this embodiment, the connecting portions click into a complementary shaped receiving portion in the steering plate 516, with a central opening and a ramp to guide the catching feature (here, the wider "top" of the T-shaped connecting portion 509) to a securing position.

Figure 6:
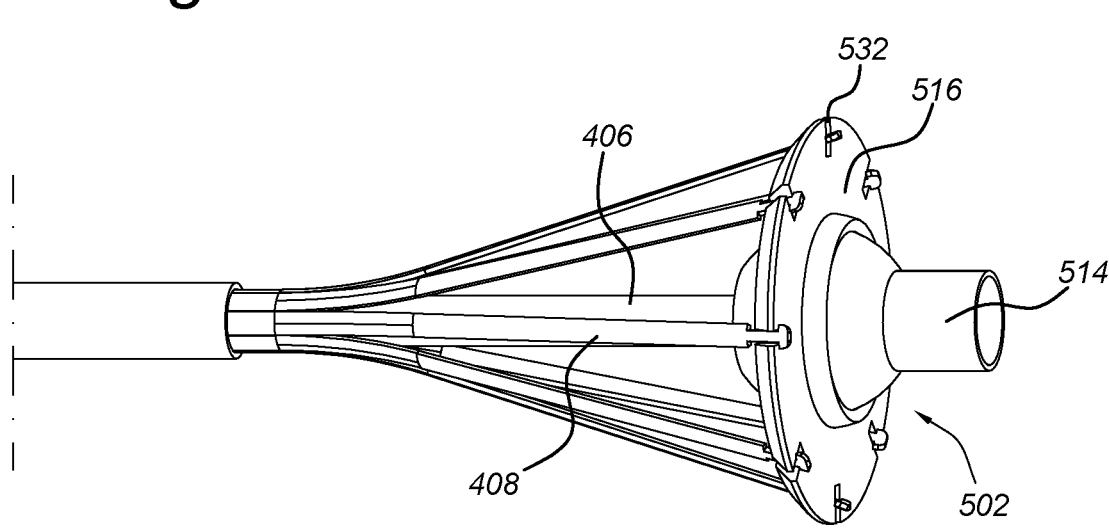
Figure 8A:
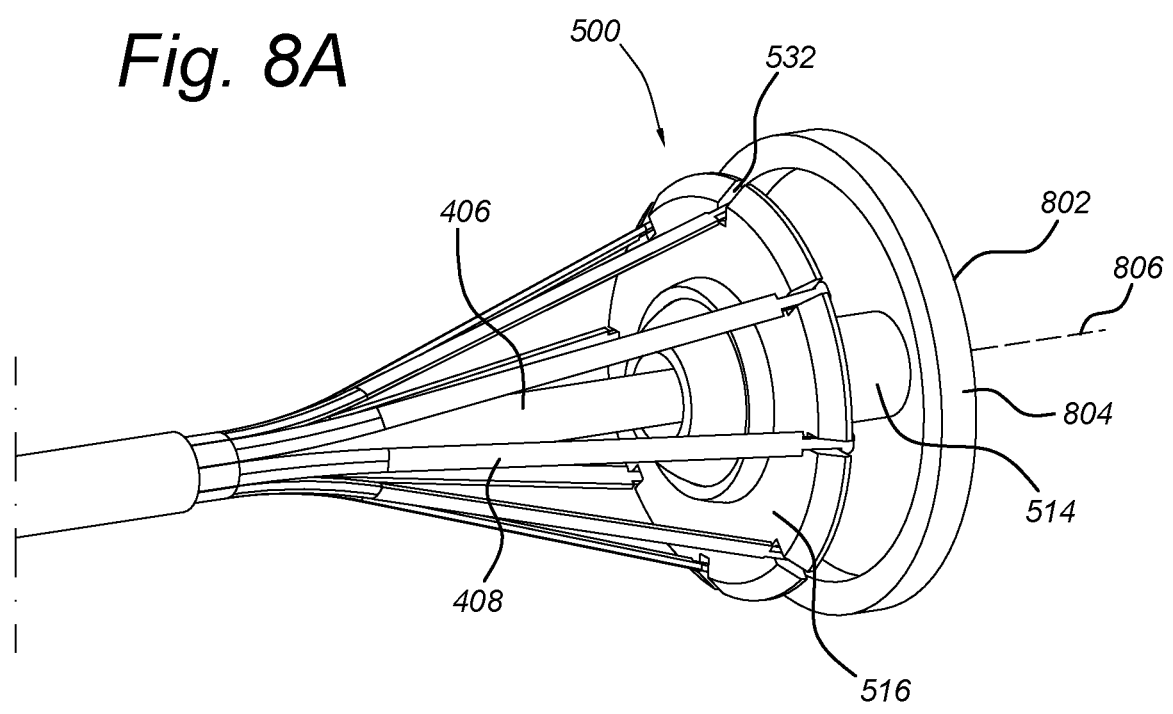
FIGS. 8A-9C show rigid elongated elements connecting to and being locked into various embodiments of locking mechanisms for a steering device.
Figure 8B:
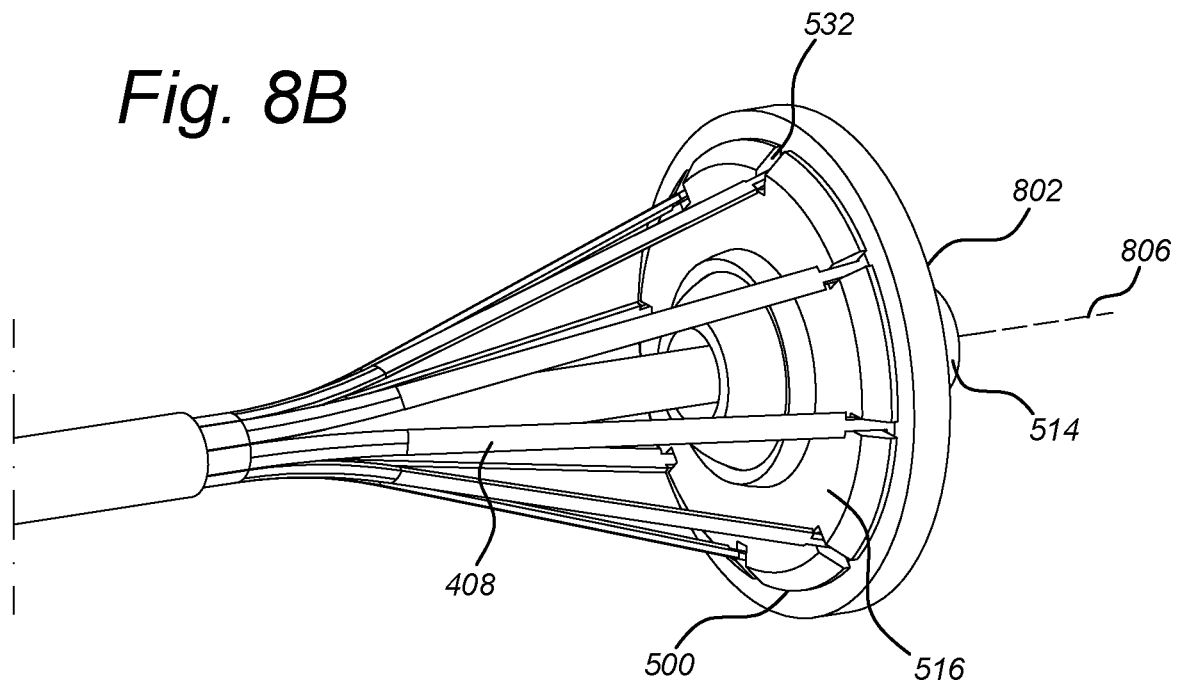

FIGS. 8A and 8B show the embodiment of FIG. 6 further comprising a locking mechanism in the form of locking plate 804. The locking mechanism 802 shown in FIGS. 8A and 8B is movable between an open position (shown in FIG. 8A) and a closed position (shown in FIG. 8B).

As it can be seen in FIG. 8A, the steering device 500 and the instrument are coupled to each other such that the elongated elements 408 are placed in the grooves 532 as it has been explained with reference to FIG. 5. FIG. 8A shows locking mechanism 802 for securing the elongated elements 408 to the steering member 504, with the locking mechanism 802 in an open position such that the elongated elements 408 can be inserted into or removed from the grooves 532. The locking mechanism 802 comprises a locking plate 804 having a circular shape with an opening in the centre such that the tube 514 of the supporting member 502 can pass through the opening. The locking plate 804 is movable axially from an open position where the elongated elements 408 are inserted or removed from the grooves 532 to a locked position where the elongated elements are secured within the openings, e.g, the locking plate 804 can be moved towards or away the steering device 500 along the central axis 806 and/or could be moved in a rotational manner.

FIG. 8B shows the embodiment of FIG. 8A where the locking mechanism has been moved from the open position shown in FIG. 8A to the locked position of FIG. 8B by moving the locking plate axially towards the instrument. This movement is until the locking plate 804 clicks against the steering plate 516 and/or connecting parts 509 of the elongated elements 408 thereby preventing the elongated elements 408 from being removed from the grooves 532 or openings 702. Locking mechanism and/or plate 804 can be in a number of different shapes and/or connect in a number of different manners as long as it can quickly and securely couple to steering plate 516 to ensure that elongated elements 408 are secured to steering plate 516. The connection also must be such that it can be quickly and easily decoupled when an operation is completed.

Figure 9A:
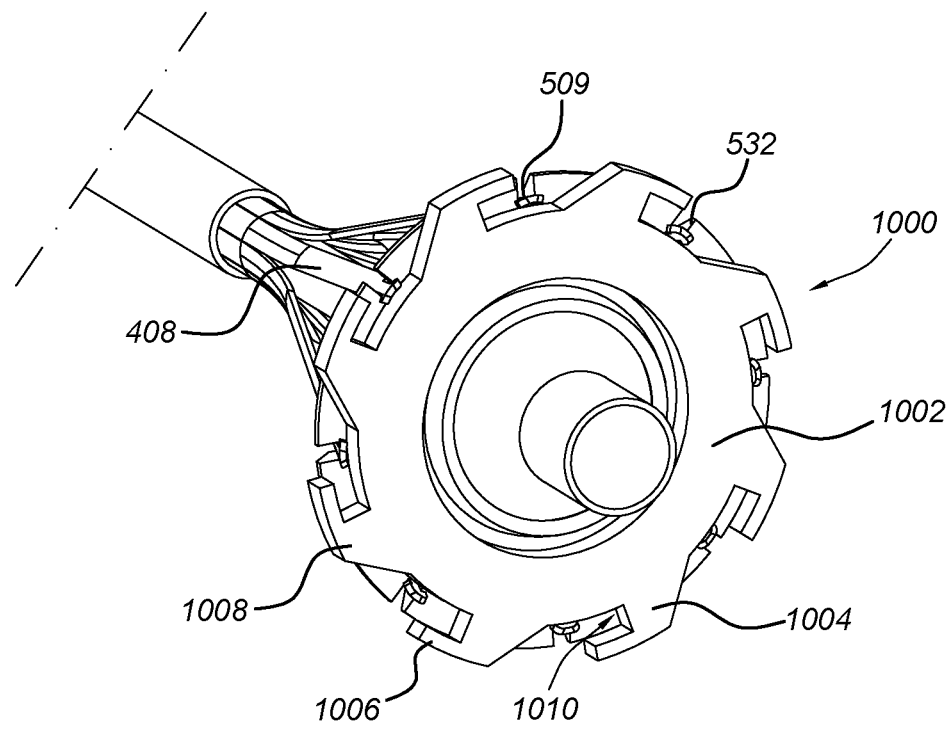
Figure 9B:
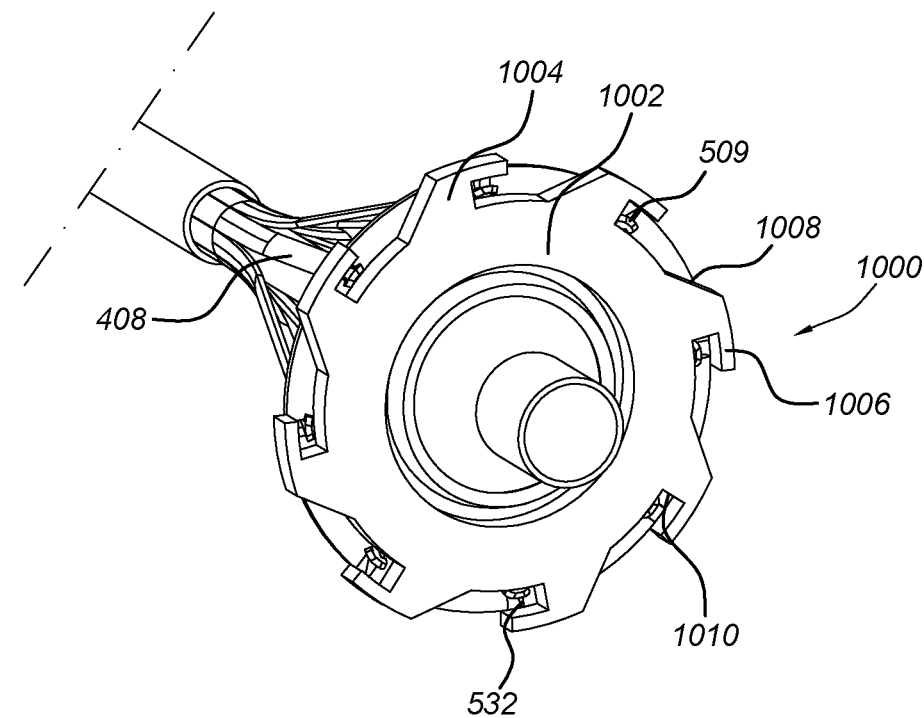
Figure 9C:
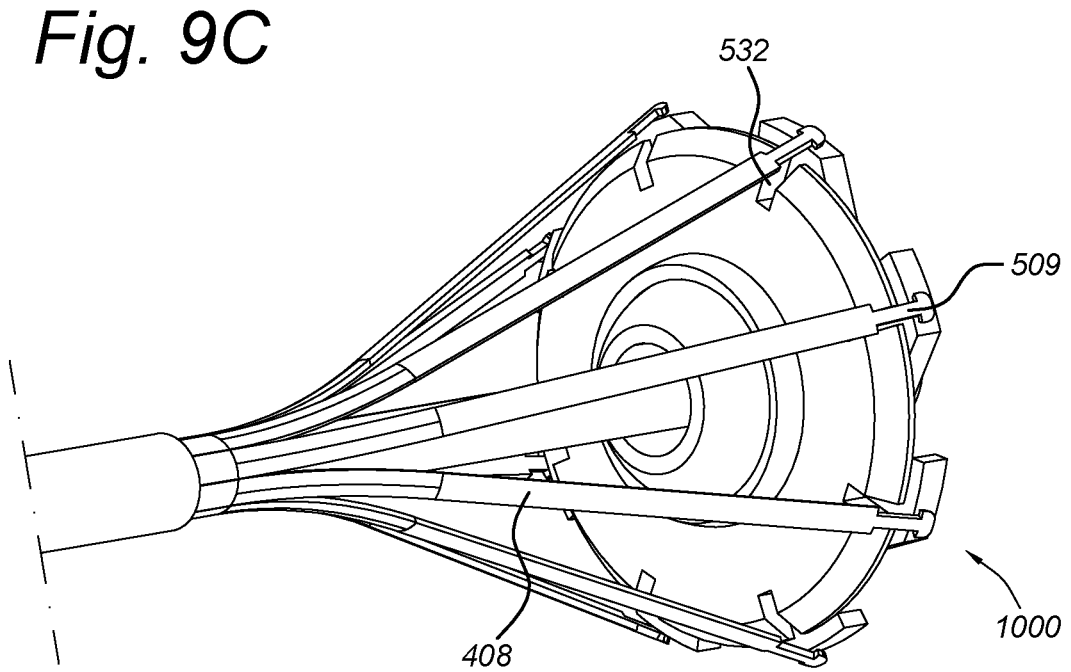

FIGS. 9A, 9B and 9C show an alternative structure for the locking mechanism of FIG. 8. The locking mechanism 1000 shown in FIGS. 9A, 9B and 9C comprise a locking plate 1002. The locking plate 1002 comprises an opening arranged such that the locking plate 1002 can be rotationally mounted with respect to steering plate 516. The locking plate 1002 comprises a plurality of protruding elements 1004 extending around an outer circumference of the locking plate. Each of the protruding elements 1004 comprises a hook-shaped side 1006 which forms a channel 1010 and an inclined side 1008.

FIG. 9A shows the locking mechanism 1000 in a position wherein each elongated element 408 is located between the hooked-shape side 1006 of a protruding element 1004 and the inclined side 1008 of the neighboring protruding element 1004 such that the elongated elements 408 can be removed from the grooves 532 of steering plate 516.

The locking plate 1002 is configured to be rotated clockwise from the open position shown in FIG. 9A to the locked position shown in FIG. 9B. The locking plate 1002 shown in FIG. 9A is rotated such that the hooked-shape side of each of the protruding elements 1004 moves towards the corresponding elongated element 408 until the elongated element is inside of a channel 1010 defined by the hooked-shape side, thereby reaching the locked position shown in FIG. 9B where the elongated elements 408 are secured in the channels 1010.

FIG. 9C shows the locking device shown in FIG. 9B after being rotated counter-clockwise from the locked position to a detached position wherein the elongated elements 408 have been removed from the grooves. By rotating the locking plate 1002 counter-clockwise, the inclined side 1008 of each of the protruding elements 1004 moves towards a corresponding elongated element 408 such that the elongated element slides on the inclined side 1008 and is pushed from its corresponding groove 532 by the inclined side 1008, thereby reaching the detached position shown in FIG. 9C where the elongated elements 408 are out of the grooves 532.

Figure 10A:
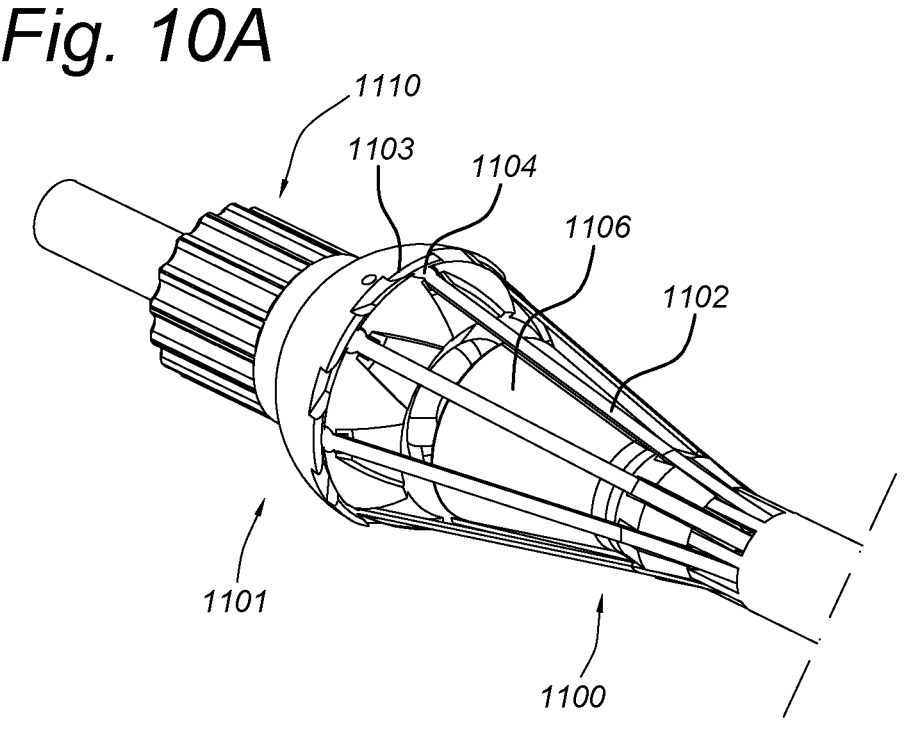
FIGS. 10A-10B shows an embodiment of a steering device with an instrument being coupled to the steering device.
Figure 10B:
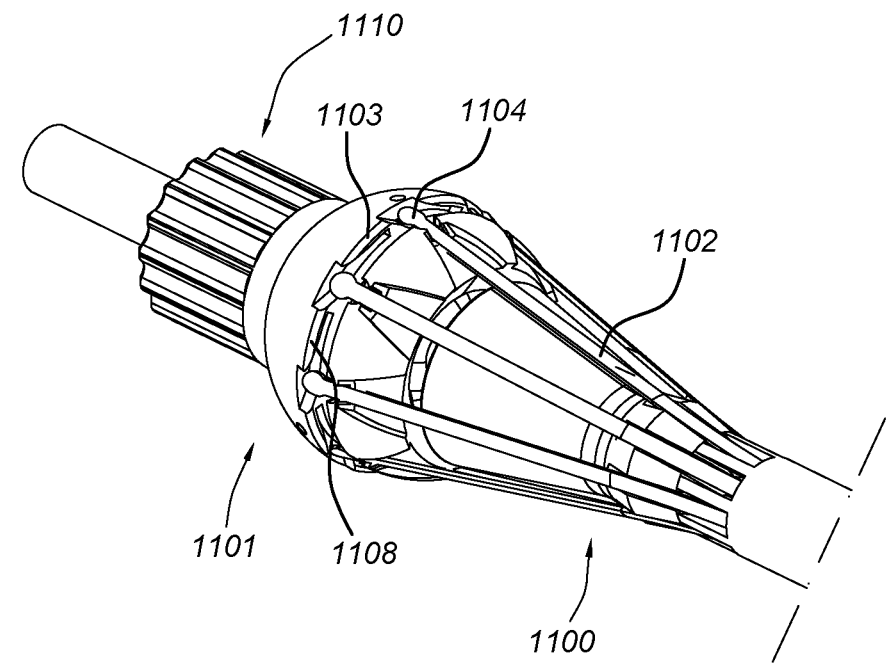
Figure 10C:
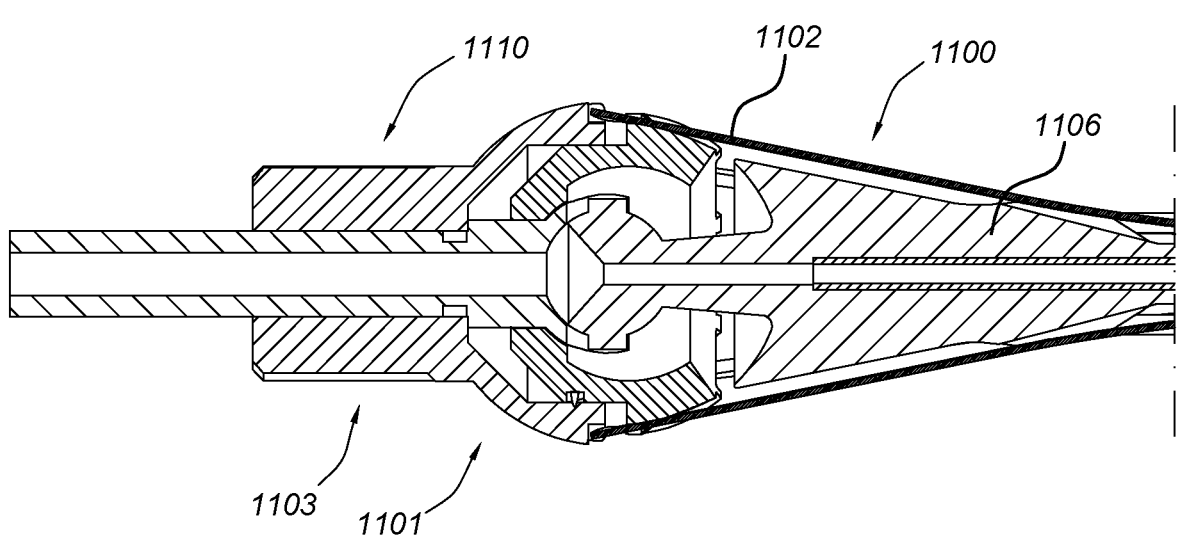
FIGS. 10C-10D show cross-sectional views of the coupling shown in FIGS. 10A-10B.
Figure 10D:
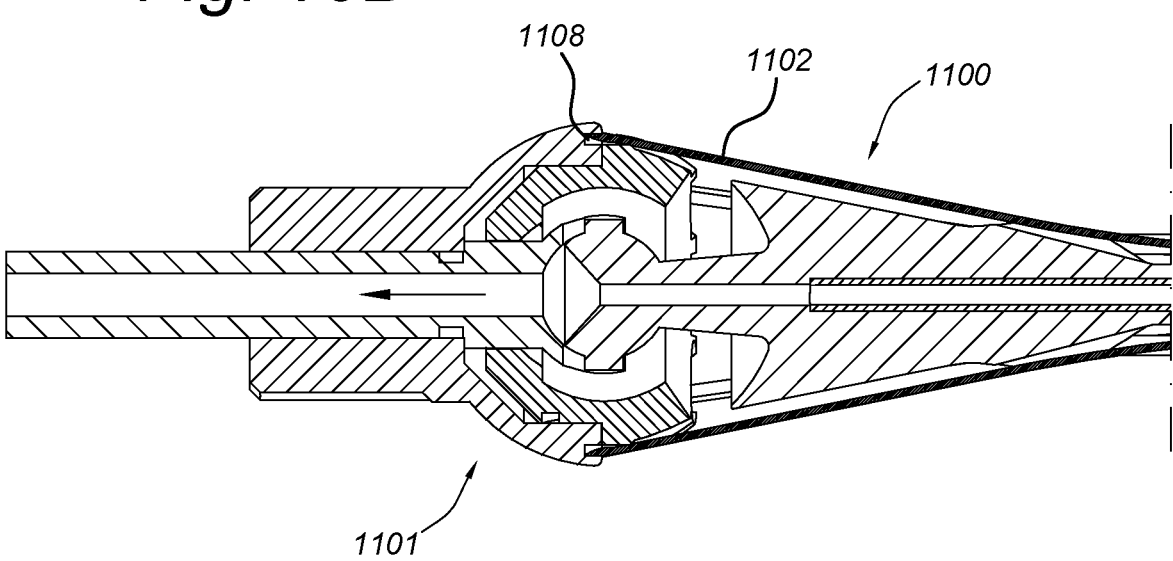

FIGS. 10A-10D show another embodiment comprising an instrument 1100, a steering device 1101 and a locking mechanism 1103. FIGS. 10A and 10D show the instrument and the steering device coupled together with the locking mechanism in an open position in FIG. 10A and in a closed position in FIG. 10B. FIGS. 10C and 10D show cross-sectional views of the instrument 1100 and steering device being coupled together.

FIGS. 10A-10D show an instrument 1000 like the instruments in FIGS. 1A-1C, with the connecting parts 1104 of the elongated elements 1102 having a circular shape instead of different shapes shown in other embodiments.

The locking mechanism 1103 shown in FIGS. 10A-10D comprises a semi spherical shape with a locking portion which operates similar to locking plate 1002 shown in FIGS. 9A-9C. Locking mechanism 1103 includes slots for receiving connecting portions 1104 of elongated elements 1102. Elongated elements 1102 can be slid into place by following the curvature of conical section 1106 leading to receiving grooves 1108. As can be seen in FIG. 10C, conical section 1106 is moved closer to locking mechanism 1103 when in an open position. This allows for easier insertion (and removal of elongated elements) into grooves 1108. When elongated elements 1102 are placed in grooves, locking mechanism 1103 is rotated to secure elongated elements in place in grooves. This is shown in FIGS. 10A and 10D. Such rotational movement to a locked position also extends conical section 1106 axially with respect to locking mechanism 1103 (see FIG. 10D). This ensures proper tensioning of elongated elements 1102, to ensure proper bending and deflection of the instrument. The instrument can be easily removed following similar steps, rotating locking mechanism 1103 to bring conical part 1106 closer to steering device 1101 and pushing elongated elements 1102 out of grooves 1108, followed by pulling instrument axially away from steering device 1101. When locking mechanism 1103 is rotated to the open position, as seen in FIG. 11B, elongated elements 1102 are pushed from grooves 1108 for easy detachment of instrument from steering device. Rotation could be performed manually, for example, through use of gripping portion 1110, or could be automated.

Figure 11:
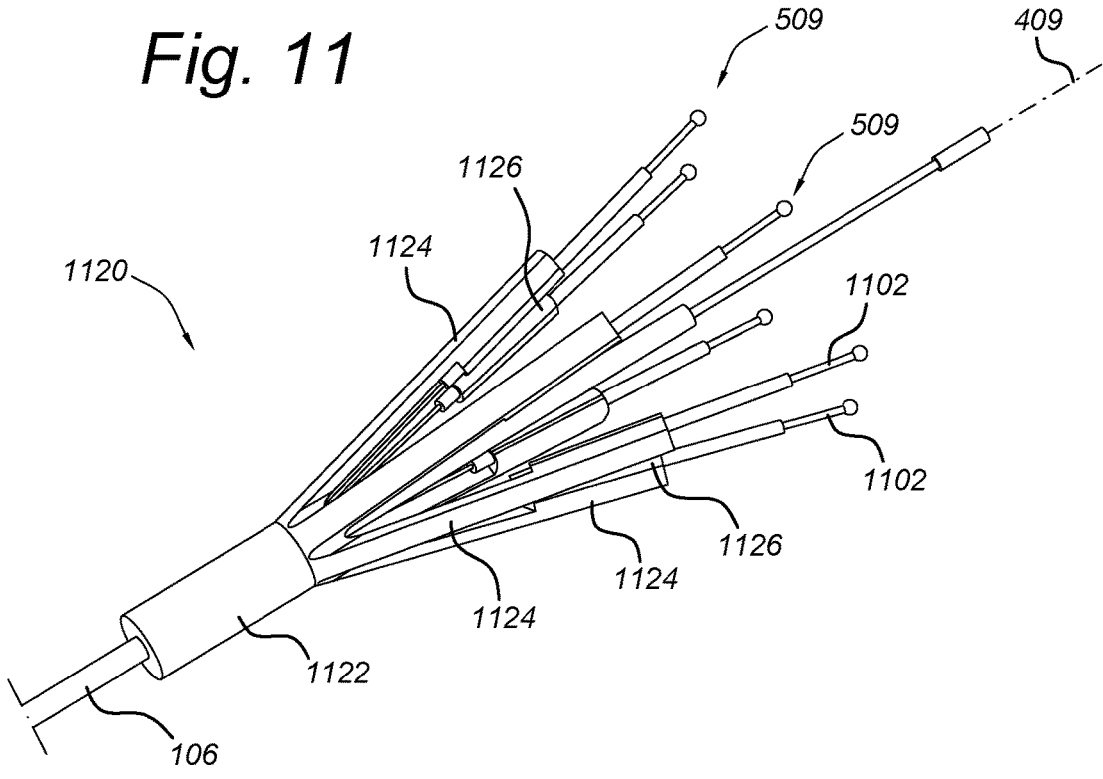
FIG. 11 shows a perspective view of an embodiment of a support part connected to an end of an instrument.
Figure 12:
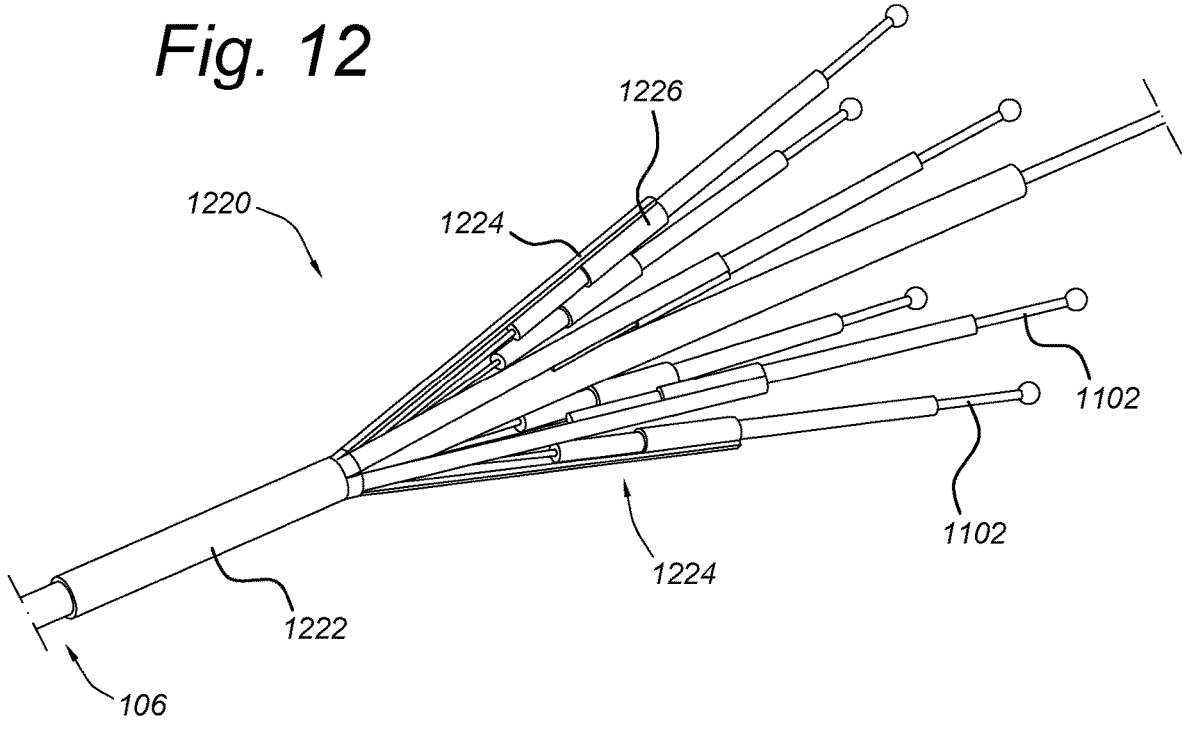
FIG. 12 shows a perspective view of a second embodiment of a support part connected to an end of an instrument.
Figure 13:
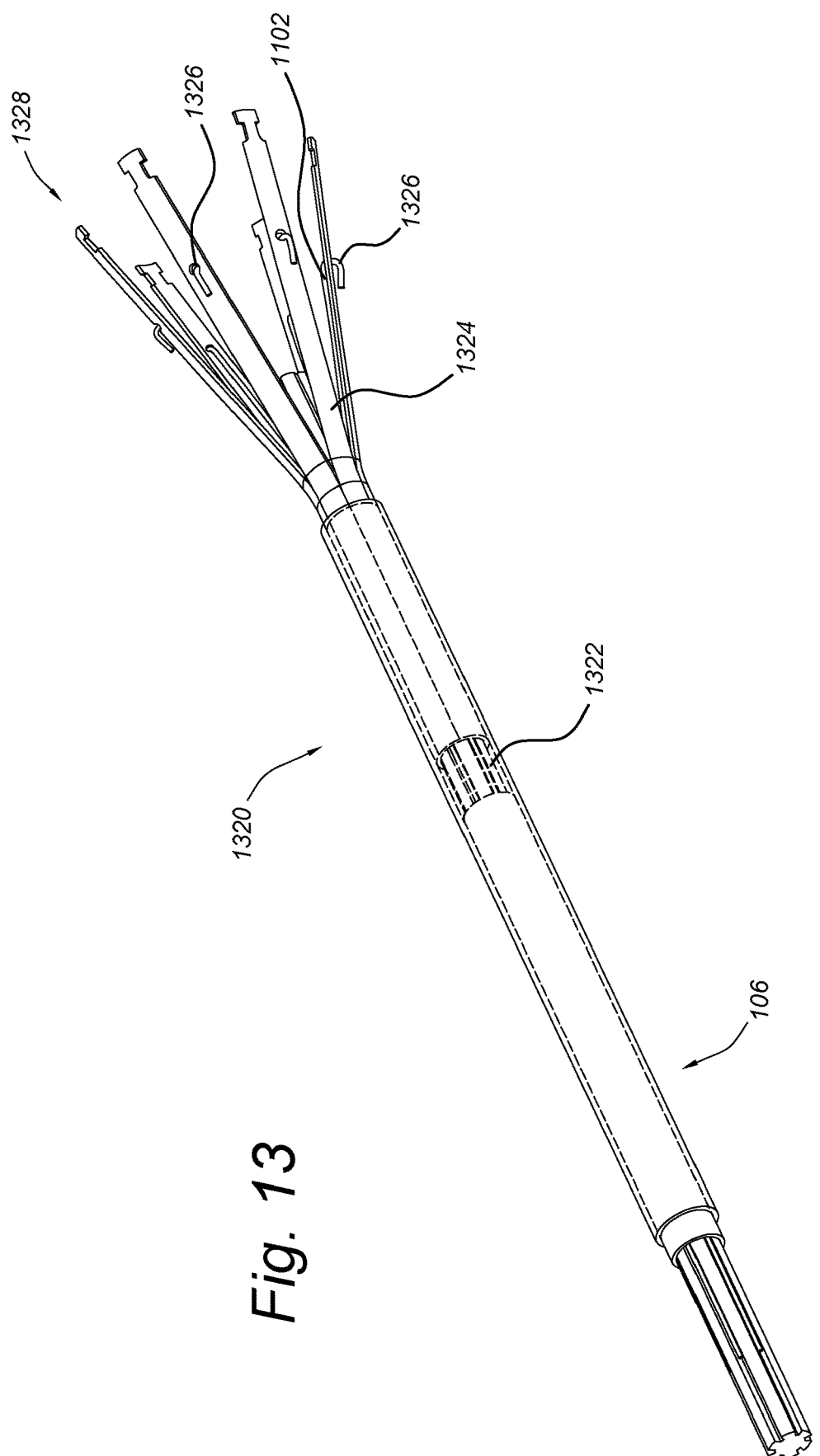
FIG. 13 shows a perspective view of a third embodiment of a support part.

FIGS. 11-13 show embodiments of support parts and support arrangements which can be used to enable connection of elongated elements to a steering mechanism (similar to the steering mechanism connections depicted in any of FIGS. 4-10D). Each support part shown can be made of metallic or plastic materials, and in some embodiments (e.g., FIG. 13) can be formed as part of the instrument 100 itself.

FIG. 11 shows a support part 1120 with a base portion 1122 and fingers 1124 rigidly connected to base portion 1122 and extending outward from a central longitudinal axis 409 running along instrument and support part 1120. Base portion 1122 secures around an outside of shaft 106 of instrument 100 such that base portion 1122 and therefore support part 1120 cannot move or shift longitudinally with respect to instrument shaft 106. Base portion 1122 can secure through a tight coupling, welding, bonding, adhesive, screws, screw-thread, spring elements, or any other means that will secure the base portion 1122 with respect to the shaft 106.

Each arm 1124 includes a collar portion 1126 to which elongated elements 1102 secure. In the embodiment shown in FIG. 11, each collar portion includes a cylinder which secures around a longitudinal element 1102, holding the element 1102 in the correct radial position/orientation and in tension. Elements 1102 are able to move longitudinally with respect to collar portion 1126 to facilitate steering. Each element 1102 has a connecting portion 509 in the form of a sphere or other mechanical feature (e.g., cylinder, hook, hole) at the end of each element 1102. The sphere and/or overall support part can facilitate connection to a steering device (which may include a steering plate) as explained and shown in relation to the previous Figures. Longitudinal tension can be maintained by frictional forces between the elongated elements 1102 and the connection to support part 1120. In other embodiments, a bonded or mechanical attachment or connection could be used to maintain longitudinal tension in the elongated elements 1102. The attachment could be configured such that it breaks after coupling to a steering device. This can be either due to activation of the steering, or a mechanism in the steering device that breaks the connection in the steering device. For example, a small amount of adhesive could be inserted at the connection of the element 1102 to the collar portion 1126. This could be physically located at a place where a part of the steering device would break the adhesive connection and/or a tensioning from connecting to the steering device would be such that it would break the adhesive connection.

FIG. 12 shows a perspective view of a second embodiment of a support part 1220 connected to an end of an instrument. Support part 1220, is similar to support part 1120, connecting to elongated elements 1102 in a similar manner, though base portion 1222 is formed as part of instrument 100 shaft 106.

The instrument shown in FIG. 12 is formed of one or more cylindrical tubes extending along and forming at least part of the shaft 106. The one or more tubes forming shaft 106 typically extend from the proximal end parts (shown) which connect to a steering device, to a distal end (see FIG. 3B). The distal end typically has some sort of instrument (e.g., scissors, gripper), though doesn't need to have an instrument.

Support part 1220 is formed from an outer tube 1222 which is split at the proximal end into fingers 1224. Fingers 1224 can be formed by cutting tube 1222 longitudinally at various points around the circumference from a proximal end for a certain length, for example 5-100 mm, preferably 10-50 mm, more preferably 15-30 mm. The fingers 1224 can then be positioned or bent outwards as shown to keep elongated elements 1102 tensioned and in position to connect to a steering plate and/or steering device (not shown in FIG. 12). This bending can be done with a device such as that shown in FIG. 4 or other devices or methods. Cutting can be done by, for example, laser cutting.

FIG. 13 shows a perspective view of a third embodiment of a support part 1320, also formed from an outer longitudinal tube 1322 which is cut longitudinally to form fingers 1324. Fingers 1324 include an opening 1326 to which elongated elements 1102 can connect. Elongated elements 1102 in the form of flexible cables connect to openings 1326 through a hook connection which secures the cables with respect to a finger 1324. Other suitable connections can include connecting through another element, laser welding, brazing and/or bonding. In this embodiment, fingers 1324 then include a connection portion 1328 which can connect to a steering plate and/or steering device. The longitudinal cuts of tube 1322 may extend only part or the whole length of the instrument, and in some embodiments can be used for transmitting steering or bending forces from a proximal end to the distal end.

The support part fingers shown in FIGS. 11-13 can be made in the configuration shown, and when the instrument is packaged, the fingers are folded or bent to a smaller diameter substantially parallel to the longitudinal axis. When unpacked and ready for coupling to a steering device, the fingers can be folded out manually or can be configured to simply spring into the position for coupling (i.e, they are tensioned to be in the positions shown in FIGS. 11-13 when at rest). The ability to have fingers move from a storage position to a use position allows for needing less space for storage and/or transportation, as well as less packaging materials due to overall smaller volumes. The use of support parts with fingers provide an easy way to support and tension elongated elements 1102 of instrument for easy coupling and then use with a steering device. Use of a support part can therefore eliminate the need for the disposable part of the instrument to include a steering plate.

In summary, having an instrument which can easily connect to and disconnect from a steering device allows for an effective instrument which is more economic. The ability to quickly and easily connect or disconnect an instrument allows for using disposable instruments, while more complicated and expensive portions are able to be reused. A secure yet simple coupling ensures that even a non-technical person could prepare the full device for an operation or could disconnect when an operation is completed. The use of a steering plate for coupling to a steering device ensures that even an elongated instrument with flexible wires or cables is ready for use and will move with precise control when coupled to the steering device.

The examples and embodiments described herein serve to illustrate rather than to limit the invention. Elements from different embodiments can be combined to form embodiments not shown in the Figures unless such combinations are non-compatible. The person skilled in the art will be able to design alternative embodiments without departing from the scope of the claims. Reference signs placed in parentheses in the claims shall not be interpreted to limit the scope of the claims. Items described as separate entities in the claims or the description may be implemented as a single item or multiple hardware items combining the features of the items described.

The term robotics has been used to describe a possible embodiment of the steering device. This term is generally used to refer to programmable machines able to carry out a series of actions autonomously, or semi-autonomously; and can include a number of components including but not limited to one or more computers, processors, memories, control units, etc. The series of actions can include movements for the instruments, including bending, rotation, etc., and the use of robotics can in some cases allow for more precise movements than manual control can generally achieve.

It is to be understood that the invention is limited by the annexed claims and its technical equivalents only. In this document and in its claims, the verb "to comprise" and its conjugations are used in their non-limiting sense to mean that items following the word are included, without excluding items not specifically mentioned. In addition, reference to an element by the indefinite article "a" or "an" does not exclude the possibility that more than one of the element is present, unless the context clearly requires that there be one and only one of the elements. The indefinite article "a" or "an" thus usually means "at least one".

US 12,582,300 B2

17

The invention claimed is:

1. A steering device for connecting to an elongated instrument; the steering device comprising:
a locking plate with a coupling to which a steering plate of the elongated instrument can secure such that the steering plate and the locking plate move together; and
a steering unit for moving the locking plate,
wherein the locking plate comprises a first plate and a second plate, the second plate being arranged at a proximal side of the first plate, the first plate having one or more openings for receiving one or more protrusions from the steering plate; and the second plate having securing slots which can receive the one or more protrusions once extending from the one or more openings and secure the one or more protrusions each by means of a bayonet fitting.

2. The steering device of claim 1, wherein the second plate rotates from an open position to allow movement of the one or more protrusions into or out of the one or more openings, to a locked position where the steering plate is secured to the locking plate and the one or more protrusions cannot move out of the one or more openings.

3. The steering device of claim 1, wherein the steering unit comprises an inner frame and an outer frame, the inner frame being connected to the outer frame at a first hinge axis about which the inner frame can rotate, and the outer frame being rotatable about a second hinge axis to enable movement of the steering plate in space.

4. The steering device of claim 1, wherein the locking plate connects to the steering unit such that the locking plate can rotate in relation to the steering unit.

5. The steering device of claim 4, wherein the locking plate connects to the steering unit with a circumferential ball bearing.

6. The steering device of claim 1, wherein the steering device comprises a robotics unit.

7. The steering device of claim 1, wherein the steering device comprises actuators to move the locking plate.

8. An elongated instrument for connecting to a steering device, the instrument comprising:
an elongated shaft with a distal end and a proximal end;
a steering plate located at the proximal end of the shaft, the steering plate movably arranged around a central supporting member rigidly connected around the shaft, the steering plate comprising a coupling for coupling the steering plate to a steering device for controlling movement of the steering plate, the steering plate comprising one or more axially extending protrusions configured for being received by one or more openings in a first portion of a locking plate of the steering device, such that the one or more protrusions can be releasably secured in the one or more openings by securing slots in a second portion of the locking plate by rotating the first portion relative to the second portion or vice versa; and
a plurality of elongated elements extending along the shaft and secured to the steering plate at the proximal end.

9. The elongated instrument of claim 8, wherein plurality of elongated elements are secured circumferentially around the steering plate.

10. The elongated instrument of claim 8, wherein the central supporting member comprises a ball-shaped element and the steering plate is connected to the ball-shaped element such that the steering plate can rotate around the ball shaped element.

11. The elongated instrument of claim 8, wherein the plurality of elongated elements extend through a plurality of openings in the steering plate and each elongated element comprises a catch at the proximal end to secure the elongated element to the steering plate.

12. The elongated instrument of claim 8, wherein the plurality of elongated elements comprises a plurality of flexible wires or cables.

13. The elongated instrument of claim 8, wherein the plurality of flexible wires or cables are tensioned between a position along the shaft and the steering plate.

14. The elongated instrument of claim 8, wherein the elongated instrument has a distal end, the plurality of elongated elements being configured for deflection of the distal end.

15. The elongated instrument of claim 8, wherein each of the one or more securing slots has a wider portion and a narrow portion.

16. The elongated instrument of claim 15, wherein the second portion of the locking plate is in an open position when the wider portion of the one or more securing slots is aligned with a corresponding one of the one or more openings of the first portion, and wherein the second portion is in a closed position when the narrow portion of the one or more securing slots is aligned with the corresponding one of the one or more openings of the first portion.

17. A medical device comprising:
a steering device and an elongated instrument, the steering device and the elongated instrument configured to be connected with one another,
the steering device comprising:
a locking plate with a coupling to which a steering plate of the elongated instrument can secure such that the steering plate and the locking plate move together, and
a steering unit for moving the locking plate,
wherein the locking plate comprises a first plate and a second plate, the second plate being arranged at a proximal side of the first plate, the first plate having one or more openings for receiving one or more protrusions from the steering plate; and the second plate having securing slots which can receive the one or more protrusions once extending from the one or more openings and secure the one or more protrusions each by means of a bayonet fitting; and
the elongated instrument comprising:
an elongated shaft with a distal end and a proximal ends,
a steering plate located at the proximal end of the shaft, the steering plate movably arranged around a central supporting member rigidly connected around the shaft, the steering plate comprising a coupling for coupling the steering plate to the steering device for controlling movement of the steering plate, the steering plate comprising one or more axially extending protrusions configured for being received by the one or more openings in the locking plate of the steering device, such that the one or more protrusions can be releasably secured in the one or more openings by the securing slots in the locking plate, and
a plurality of elongated elements extending along the shaft and secured to the steering plate at the proximal end.

* * * * *